US012661337B2

(12) United States Patent
Voudouris

(10) Patent No.: US 12,661,337 B2
(45) **Date of Patent: *Jun. 23, 2026**

(54) BENDAMUSTINE PHARMACEUTICAL COMPOSITIONS

(71) Applicant: Vasilios Voudouris, Sacramento, CA (US)

(72) Inventor: Vasilios Voudouris, Sacramento, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 18/665,804

(22) Filed: May 16, 2024

(65) Prior Publication Data

US 2024/0299363 A1 Sep. 12, 2024

Related U.S. Application Data

(63) Continuation of application No. 18/200,980, filed on May 23, 2023, now abandoned, which is a continuation of application No. 17/532,874, filed on Nov. 22, 2021, now Pat. No. 11,701,344, which is a continuation of application No. 16/999,908, filed on Aug. 21, 2020, now abandoned, which is a continuation of application No. 15/815,578, filed on Nov. 16, 2017, now Pat. No. 10,786,486, which is a continuation of application No. 14/466,765, filed on Aug. 22, 2014, now Pat. No. 9,849,115.

(60) Provisional application No. 61/870,609, filed on Aug. 27, 2013.

(51) Int. Cl.

| | |
|---|---|
| ***A61K 31/4184*** | (2006.01) |
| ***A61K 9/00*** | (2006.01) |
| ***A61K 9/16*** | (2006.01) |

(52) U.S. Cl.

CPC ........ *A61K 31/4184* (2013.01); *A61K 9/0095* (2013.01); *A61K 9/16* (2013.01); *A61K 9/1617* (2013.01); *A61K 9/1623* (2013.01); *A61K 9/1635* (2013.01); *A61K 9/1641* (2013.01); *A61K 9/1652* (2013.01); *A61K 9/1682* (2013.01); *A61K 9/1694* (2013.01)

(58) Field of Classification Search

CPC .... A61K 31/4184; A61K 9/0095; A61K 9/16; A61K 9/1617; A61K 9/1623; A61K 9/1635; A61K 9/1641; A61K 9/1652; A61K 9/1682; A61K 9/1694; A61P 35/00; A61P 35/02; A61P 37/06

See application file for complete search history.

(56) References Cited

U.S. PATENT DOCUMENTS

| | | | |
|---|---|---|---|
| 8,344,006 | B2 | 1/2013 | Drager et al. |
| 8,436,190 | B2 | 5/2013 | Brittain et al. |
| 8,445,524 | B2 | 5/2013 | Courvoisier et al. |
| 8,461,350 | B2 | 6/2013 | Brittain et al. |
| 8,609,707 | B2 | 12/2013 | Palepu et al. |
| 8,609,863 | B2 | 12/2013 | Brittain et al. |
| 8,669,279 | B2 | 3/2014 | Cooper et al. |
| 8,791,270 | B2 | 7/2014 | Brittain et al. |
| 8,802,149 | B2 | 8/2014 | Gordon et al. |
| 8,883,836 | B2 | 11/2014 | Cooper et al. |
| 8,895,756 | B2 | 11/2014 | Brittain et al. |
| 9,061,011 | B1 | 6/2015 | Voudouris |
| 9,320,730 | B2 | 4/2016 | Voudouris |
| 9,849,115 | B2 | 12/2017 | Voudouris |
| 10,786,486 | B2 | 9/2020 | Voudouris |
| 11,701,344 | B2 | 7/2023 | Voudouris |
| 2003/0105141 | A1 | 6/2003 | Gao et al. |
| 2003/0129250 | A1 | 7/2003 | Batycky et al. |
| 2003/0161846 | A1 | 8/2003 | Holmberg et al. |
| 2006/0159713 | A1 | 7/2006 | Brittain et al. |
| 2009/0130198 | A1 | 5/2009 | Hao et al. |
| 2009/0285905 | A1 | 11/2009 | Gordon et al. |
| 2010/0273730 | A1 | 10/2010 | Hsu et al. |
| 2012/0003305 | A1 | 1/2012 | Colledge et al. |
| 2012/0003309 | A1 | 1/2012 | Colledge et al. |
| 2012/0157505 | A1 | 6/2012 | LaBell et al. |
| 2013/0210879 | A1 | 8/2013 | Palepu et al. |
| 2013/0253025 | A1 | 9/2013 | Sundaram |
| 2014/0142153 | A1 | 5/2014 | Kocherlakota et al. |
| 2014/0148490 | A1 | 5/2014 | Brittain et al. |
| 2014/0378407 | A1 | 12/2014 | Khattar et al. |
| 2015/0065549 | A1 | 3/2015 | Voudouris |
| 2015/0140085 | A1 | 5/2015 | Goldstein |
| 2018/0071263 | A1 | 3/2018 | Voudouris |
| 2021/0008036 | A1 | 1/2021 | Voudouris |
| 2022/0079923 | A1 | 3/2022 | Voudouris |
| 2023/0310381 | A1 | 10/2023 | Voudouris |

FOREIGN PATENT DOCUMENTS

| | | | |
|---|---|---|---|
| CN | 1887261 | A | 1/2007 |
| EP | 2641592 | A1 | 9/2013 |
| WO | WO 2011/103150 | A2 | 8/2011 |

(Continued)

OTHER PUBLICATIONS

International Search Report and Written Opinion issued in PCT/US2014/52341, mailed Feb. 10, 2015, 13 pages.

International Search Report and Written Opinion mailed May 15, 2015, for PCT application No. PCT/US2015/018725, filed Mar. 4, 2015, 12 pages.

Brem et al. Placebo-controlled trial of safety and efficacy of intraoperative controlled delivery by biodegradable polymers of chemotherapy for recurrent gliomas. The Lancet, vol. 345, pp. 1008-1012. (Year 1995).

(Continued)

*Primary Examiner* — Jessica Worsham

(74) *Attorney, Agent, or Firm* — Nixon Peabody LLP

(57) ABSTRACT

Provided herein are pharmaceutical formulations of dry-powder bendamustine suitable for pharmaceutical use. Also provided are methods of producing dry-powder bendamustine. The pharmaceutical formulations can be used for any disease that is sensitive to treatment with bendamustine, such as neoplastic diseases.

1 Claim, 14 Drawing Sheets

(56) References Cited

FOREIGN PATENT DOCUMENTS

| | | | |
|---|---|---|---|
| WO | WO 2013/102920 | A1 | 7/2013 |
| WO | WO 2013/139991 | A1 | 9/2013 |

OTHER PUBLICATIONS

Chemical Abstracts Service registry No. 16506-27-7 (bendamustine), 1 page.
Chemical Abstracts Service registry No. 3543-75-7 (bendamustine hydrochloride), 1 page.
Cephalon's Proposed Findings Of Fact And Conclusions Of Law For U.S. Pat. Nos. 8,436,190, 8,609,863, 8,791,270, and 8,895,756 in Case 1:13-cv-02046-GMS Document 455 filed Jan. 29, 2016, 64 pages.
Cheson et al., Bendamustine: Rebirth of an Old Drug (2009) Journal of Clinical Oncology 27:1492-1501.
Gwen B. Bauer et al., Specificity and kinetics of interstrand and intrastrand bifunctional alkylation by nitrogen mustards at a G-G-C sequence (1997) Nucleic Acids Research vol. 25, No. 6, pp. 1211-1218.
Letter from Cephalon to FDA on Dilution problems dated Mar. 8, 2013, 2 pages.
Memorandum before order re Case 1: 13-cv-02046-GMS Document 472 filed Jun. 10, 2016, 24 pages.
Munro, Nancy B. et al., The Sources, Fate, and Toxicity of Chemical Warfare Agent Degradation Products (1999) Environmental Health Perspectives 107(12) pp. 933-974.
Ribomustin® (2005) Fachinformation (Zusammenfassung der Merkmale des Arzneimittels/SPC), 4 pages, in German language.
Strickley, R.G., Solubilizing Excipients in Oral and Injectable Formulations, Pharmaceutical Research, 2004, 21(2):201-230.
Zhang et al., Self-Assembled Nanoparticles of Amphiphilic Twin Drug from Floxuridine and Bendamustine for Cancer Therapy. Molecular Pharmaceutics, 2015, vol. 12, pp. 2328-2336.

Spray drying steam with a 1-liquid-phase nozzle

Details of a 1-liquid-phase nozzle

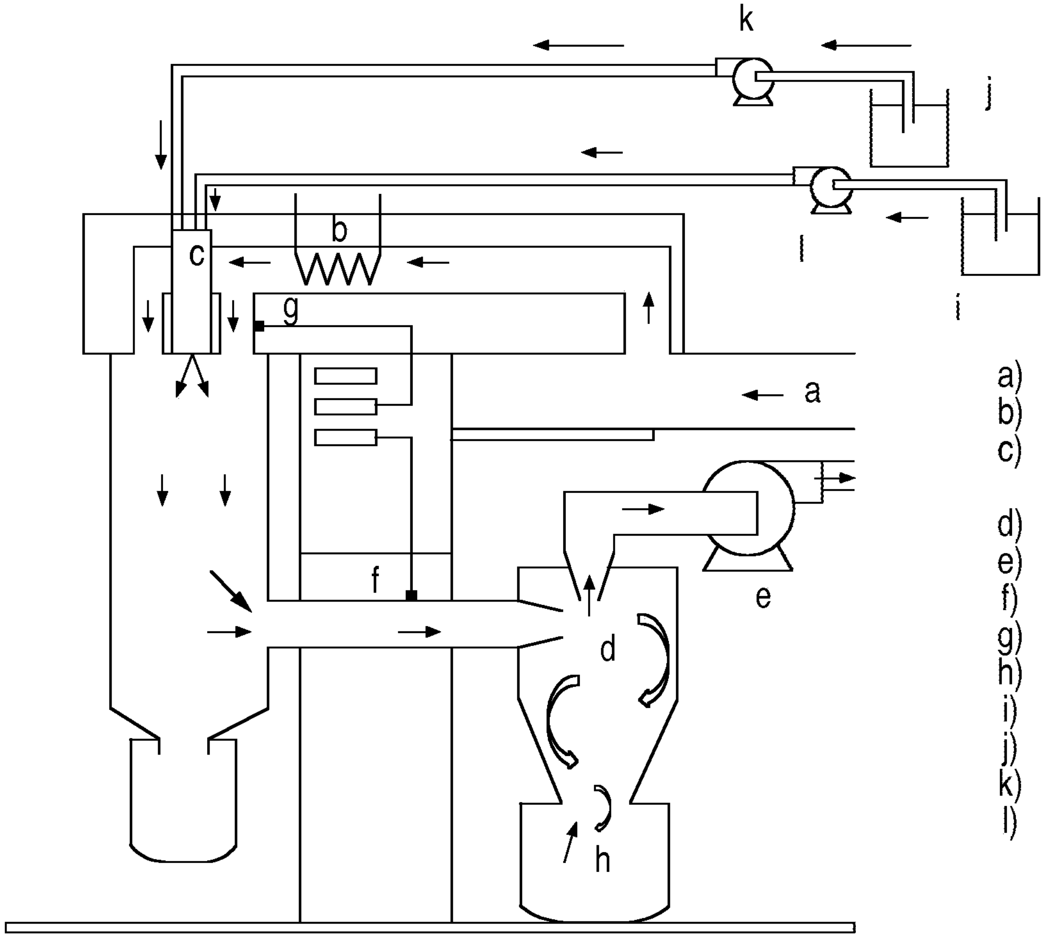

a) Process gas in
b) Process gas heat exchanger
c) Flow stabilized inlet to the drying
(details in Fig. 4)
d) Cyclone. Product is separated fr
e) Air blower
f) Temperature indicator of incomir
g) Temperature indicator of outgoin
h) Collection container
i) Non-Aqueous bendamustine pre-drying solution
j) Aqueous excipient pre-drying solution
k) Pump
l) Pump Spray drying steam with a 2-liquid-phase nozzle

FIG. 3

Details of a 2-liquid-phase nozzle

XRPD DIFFRACTOGRAM FOR BATCH 3

XRPD DIFFRACTOGRAM FOR BATCH 4

DEGREE 2θ

XRPD DIFFRACTOGRAM FOR BATCH 5

XPRD DIFFRACTOGRAM FOR BATCH 5 AT t = 2 MONTHS

OPTICAL MICROSCOPY FOR BATCH 5

XPRD DIFFRACTOGRAM FOR BATCH 5 AT t = 2 MONTHS

BENDAMUSTINE PHARMACEUTICAL COMPOSITIONS

CROSS-REFERENCE TO RELATED APPLICATIONS

This application is a continuation of U.S. patent application Ser. No. 18/200,980, filed May 23, 2023, which is a continuation of U.S. patent application Ser. No. 17/532,874, filed Nov. 22, 2021, now U.S. Pat. No. 11,701,344, which is a continuation of U.S. patent application Ser. No. 16/999,908, filed Aug. 21, 2020, now abandoned, which is a continuation of U.S. patent application Ser. No. 15/815,578, filed Nov. 16, 2017, now U.S. Pat. No. 10,786,486, which is a continuation of U.S. patent application Ser. No. 14/466,765, filed Aug. 22, 2014, now U.S. Pat. No. 9,849,115, which claims priority under 35 U.S.C. § 119 (e) to U.S. Provisional Patent Application No. 61/870,609, filed Aug. 27, 2013, the contents of each of which are incorporated herein by reference in their entirety.

FIELD

Provided herein are pharmaceutical compositions for the treatment of various disease states, especially neoplastic diseases and autoimmune diseases. Useful pharmaceutical compositions comprise nitrogen mustards, particularly the nitrogen mustard bendamustine, e.g., bendamustine HCl.

BACKGROUND

The following description includes information that can be useful in understanding the present embodiments. It is not an admission that any such information is prior art, or relevant, to the presently claimed embodiments, or that any publication specifically or implicitly referenced is prior art.

Because of their high reactivity in aqueous solutions, nitrogen mustards can be difficult to formulate as pharmaceuticals, and they are often supplied for administration in a lyophilized form that requires reconstitution, usually in water, by skilled hospital personal prior to administration. Once in aqueous solution, nitrogen mustards are subject to degradation by hydrolysis; thus, the reconstituted product should be administered to a patient as soon as possible after its reconstitution.

Bendamustine, 4-{5-[Bis(2-chloroethyl)amino]-1-methyl-2-benzimidazolyl} butyric acid, includes a benzimidazole ring and an active nitrogen mustard, according to Formula I.

Formula I

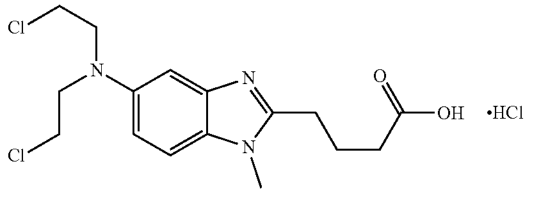

Bendamustine is also identified by the following: 5-(Bis(2-chloroethyl)amino)-1-methyl-2-benzimidazolebutyric acid; HSDB 7763; SDX105; SDX-105; and UNII-9266D9P3PQ. Bendamustine is further identified by the Chemical Abstracts Service registry numbers 16506-27-7 and 3543-75-7 (hydrochloride).

Bendamustine was initially synthesized in 1963 in the German Democratic Republic (GDR) and was available from 1971 to 1992 in that location under the name Cytostasan®. Since that time, it has been marketed in Germany under the tradename Ribomustin®. It has been widely used in Germany to treat chronic lymphocytic leukemia, Hodgkin's disease, non-Hodgkin's lymphoma, multiple myeloma, and breast cancer.

Due to its degradation in aqueous solutions (like other nitrogen mustards), bendamustine is currently supplied as a lyophilized product. The current lyophilized formulations of bendamustine (Ribomustin®, Treanda®) contain bendamustine hydrochloride and mannitol in a sterile lyophilized form as a white powder for intravenous use following reconstitution. The finished lyophilisate can be unstable when exposed to light. Therefore, the product is stored in brown or amber-colored glass bottles. The current lyophilized formulations of bendamustine contain degradation products that can occur during manufacturing of the drug substance and/or during the lyophilization process to make the finished drug product.

Currently the bendamustine drug product Ribomustin® is formulated as a lyophilized powder for injection with 100 mg of drug per 50 mL vial or 25 mg of drug per 20 mL vial. The vials are opened and reconstituted as close to the time of patient administration as possible. The product is reconstituted with 40 mL (for the 100 mg presentation) or 10 mL (for the 25 mg presentation) of Sterile Water for Injection. The reconstituted product is further diluted into 500 mL, q.s., 0.9% Sodium Chloride for Injection. The route of administration is by intravenous infusion over 30 to 60 minutes.

Following reconstitution with Sterile Water for Injection, vials of Ribomustin® are stable for a period of 7 hours under room temperature storage or for 6 days upon storage at 2-8° C. The 500 mL admixture solution must be administered to the patient within 7 hours of vial reconstitution (assuming room temperature storage of the admixture).

Currently, the bendamustine drug product Treanda® is formulated as a lyophilized powder for injection with 100 mg of drug per 50 mL vial or 25 mg of drug per 20 mL vial. The vials are opened and reconstituted as close to the time of patient administration as possible. The product is reconstituted with 20 mL (for the 100 mg presentation) or 5 mL (for the 25 mg presentation) of Sterile Water for Injection. The reconstituted product is further diluted into 500 mL, q.s., 0.9% Sodium Chloride for Injection. As an alternative to 0.9% Sodium Chloride for Injection, 2.5% Dextrose/0.45% Sodium Chloride for Injection can be considered. The route of administration is by intravenous infusion over 30 to 60 minutes.

Following reconstitution with Sterile Water for Injection, vials of Treanda® are stable for a period of 3 hours under room temperature storage (15-30° C.) or for 24 hrs upon storage at 2-8° C. The 500 mL admixture solution must be administered to the patient within this period.

The reconstitution of Ribomustin® lyophilized powder is difficult. Reports from the clinic indicate that reconstitution can require at least fifteen minutes and can require as long as thirty minutes. The reconstitution of Treanda® is also difficult. Treanda®'s label indicates a 5 minute requirement for reconstitution. Besides being burdensome and time-consuming for the healthcare professional responsible for reconstituting the product, the lengthy exposure of bendamustine to water during the reconstitution process increases the potential for loss of potency and impurity formation due to the hydrolysis of the product by water.

Thus, a need exists for dry powder formulations of bendamustine that are easier to reconstitute and which have a better impurity profile than the current lyophilisate (lyophilized powder) formulations of bendamustine.

SUMMARY

Provided herein are stable compositions of nitrogen mustards, in particular, dry-powder bendamustine and methods of their use in treatment of various disease states, for instance neoplastic diseases and autoimmune diseases.

In another aspect, provided herein are solid dispersions comprising bendamustine. The solid dispersions can show greater stability and fewer impurities. In certain embodiments, the solid dispersions comprise a limited amount of impurities. In certain embodiments, the solid dispersions provide a limited amount of impurities, for instance, after storage.

In one aspect, provided herein are pharmaceutical compositions comprising a solid dispersion of bendamustine. The pharmaceutical compositions can show greater stability and fewer impurities. In certain embodiments, the pharmaceutical compositions comprise a limited amount of impurities. In certain embodiments, the pharmaceutical compositions provide a limited amount of impurities, for instance, after storage.

While not intending to be bound by any particular theory of operation, it is believed that the increased stability of the compositions provided herein results from the limited aqueous exposure of the active components during manufacture and storage as well as the thermodynamic properties of the solid dispersions and the differences in the drying and solid state formation mechanisms between lyophilization and alternative forms of drying. In particular, provided herein are methods of making the compositions with remarkably little, if any, exposure to aqueous substances.

In another aspect, provided herein are pharmaceutical dosage forms comprising one or more of the pharmaceutical compositions. The pharmaceutical dosage forms typically comprise one or more of the pharmaceutical compositions in an amount sufficient to provide a desired dose of the active component to a patient in need thereof. The pharmaceutical dosage forms typically further comprise containers and/or packaging useful for storing, transporting and/or reconstituting the pharmaceutical composition.

In another aspect, provided herein are methods of preparing a bendamustine dry powder. The methods are useful for making the dry powders and pharmaceutical compositions provided herein. In certain embodiments, the methods comprise drying a solution of bendamustine in a non-aqueous solvent. In certain embodiments, the methods comprise combining, in a continuous manner, bendamustine in a non-aqueous solvent with one or more pharmaceutically acceptable excipients in an aqueous solution. Remarkably, these methods can provide bendamustine dry powders and bendamustine pharmaceutical compositions with the advantageous purity and stability described herein.

In another aspect, provided herein are formulations useful, for example, in the methods of preparing. In certain embodiments, the formulations comprise bendamustine, a aqueous excipient and a non-aqueous solvent. In certain embodiments, provided herein are sets of formulations useful, for example, in methods of preparing bendamustine pharmaceutical compositions and bendamustine dry powders. In certain embodiments, one formulation of the set comprises an aqueous excipient in an aqueous solution, and another formulation in the set comprises bendamustine in a non-aqueous solvent. The formulations in the set can be combined, for instance in a continuous manner, to produce a bendamustine dry powder or a bendamustine pharmaceutical composition.

The pharmaceutical compositions and dry powders are useful for the treatment of proliferative and autoimmune conditions. Accordingly, in another aspect, provided herein are methods of treating medical conditions in patients in need thereof. The methods typically comprise administering a pharmaceutical composition provided herein to a patient in need thereof. The pharmaceutical composition is typically reconstituted in aqueous solution for intravenous administration to the patient. Conditions that can be treated include proliferative diseases and autoimmune diseases.

BRIEF DESCRIPTION OF THE FIGURES

FIG. 3 provides a spray drying system a 2-liquid-phase nozzle with mixing within the nozzle useful for producing bendamustine dry-powder.

DESCRIPTION OF EXEMPLARY EMBODIMENTS

Figure 1:
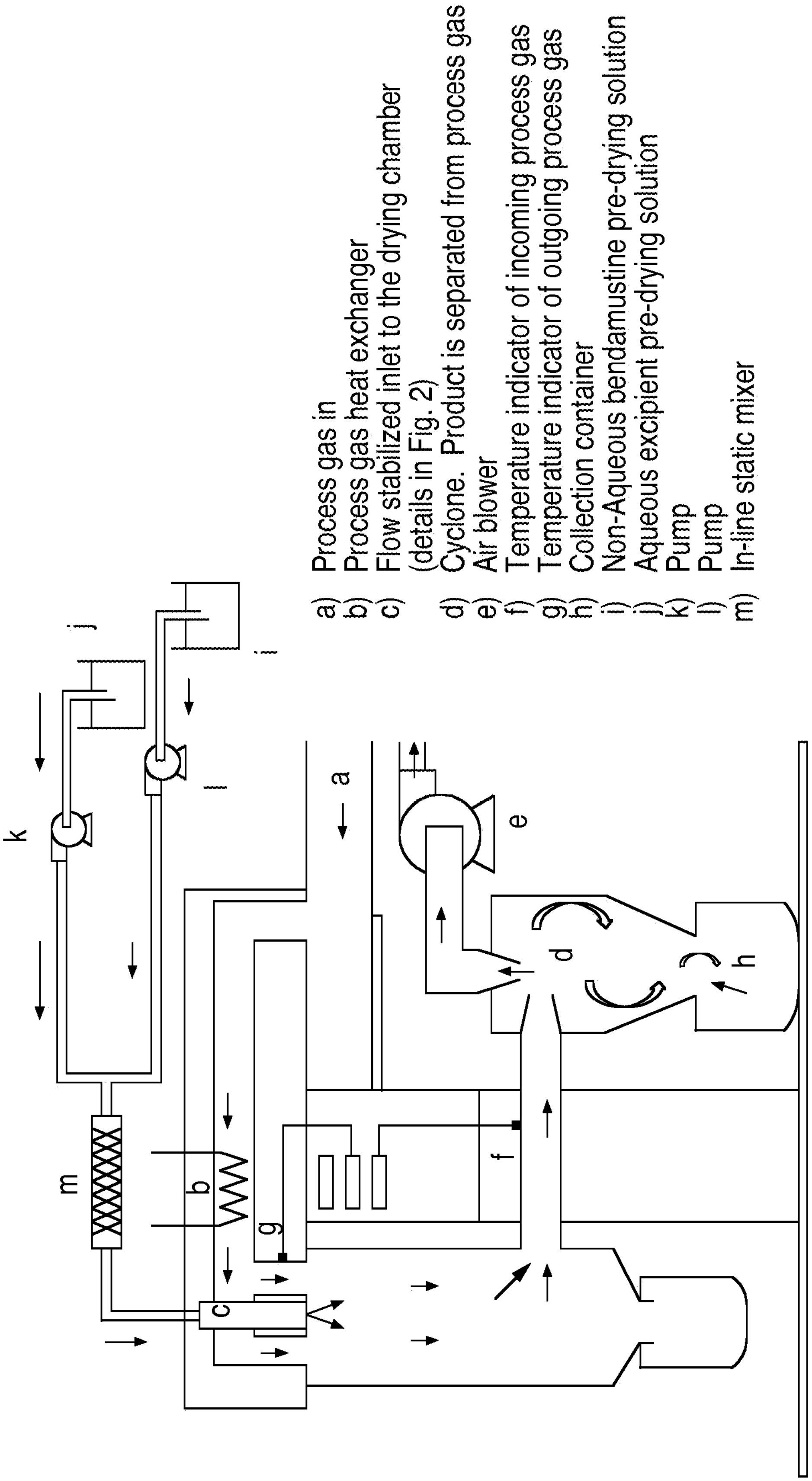
FIG. 1 provides a spray drying system with in-line static mixing and a 1-liquid-phase nozzle useful for producing bendamustine dry-powder.
Figure 2:
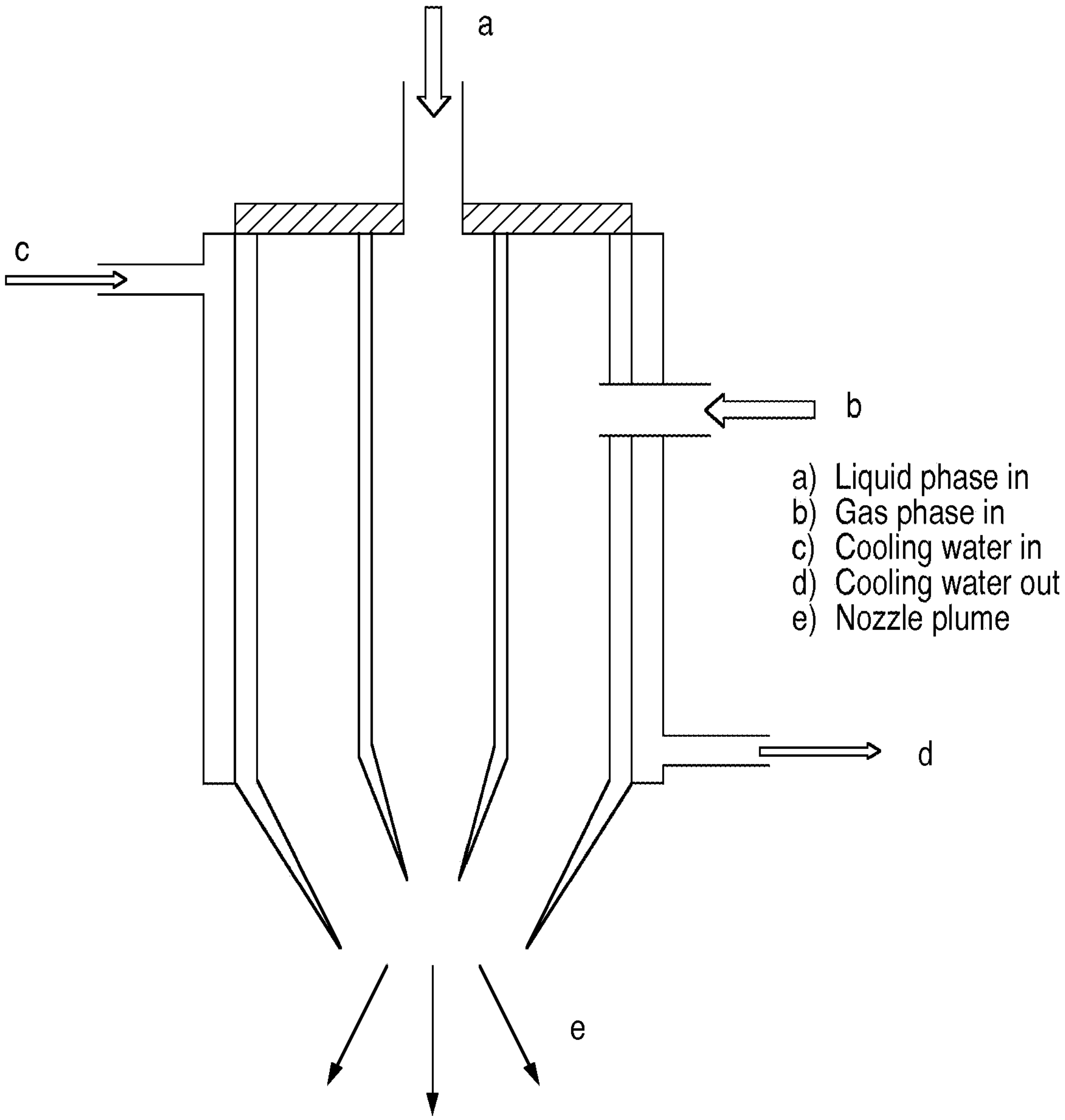
FIG. 2 provides a detailed view of a 1-liquid-phase spray nozzle useful for producing bendamustine dry-powder.

Provided herein are bendamustine compositions and methods useful for treating a proliferative disease in a subject. Further provided are dosage forms useful for such methods.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "solid dispersion" refers to a solid product comprising a polymeric matrix and a drug. The matrix can be either crystalline or amorphous. The drug can be dispersed molecularly, in amorphous particles, for instance clusters, or in crystalline particles. In certain embodiments, a solid dispersion is in any of the following forms, or any combination thereof: a) a simple eutectic mixture, b) a solid solution (continuous, discontinuous, substitutional, interstitial, amorphous), c) a glass solution, and d) an amorphous precipitation in a crystalline carrier. In certain embodiments, certain more complex combinations can be encountered, i.e. in the same sample some molecules are present in clusters while some are molecularly dispersed.

It is well known in persons having ordinary skill in the art of metallurgy, geology, chemistry and chemical engineering that physical, morphological, mechanical and other properties of solid dispersion can depend not only on composition but also on the method with which the dispersion is obtained (e.g., via rapid quenching from a hot melt or through cycles of aging). This is mainly due to the impact these dynamic events have on the solid lattice and surface thermodynamics of the ensuing dispersions. For instance, solid dispersions of a drug product with the same composition but obtained through different production methods, could have different solubility such that a more thermodynamically stable solid dispersion is less soluble than a less thermodynamically stable solid dispersion. Solid dispersions can also differ in properties such as shelf-life, bioavailability, morphology, density, color, and compressibility. Accordingly, variation of the characteristics of a solid dispersion of a drug product is one of many ways in which to modulate the physical and pharmacological properties thereof.

The term "substantially free of" or "substantially in the absence of" with respect to degradants refers to a composition that includes at least 85% or 90% by weight, in certain embodiments 95%, 98%, 99% or 100% by weight, of a designated component of the composition. In certain embodiments, in the methods and compounds provided herein, the compositions are substantially free of degradants.

As used herein, the term "formulate" refers to the preparation of a drug, e.g., bendamustine, in a form suitable for administration to a mammalian patient, preferably a human. Thus, "formulation" can include the addition of pharmaceutically acceptable excipients, diluents, or carriers.

As used herein, the term "dry-powder" or "dry-powder preparation" refers to any solid material obtained by continuous drying, e.g., spray-drying or fluidized bed drying of a non-aqueous solution or of an aqueous solution or of a combination of an aqueous and non-aqueous solutions. The non-aqueous solution can contain one or more non-aqueous solvent(s). Preferably, a dry-powder preparation is one in which the solid material is obtained by spray drying a solution composed of one or more non-aqueous solvents, more preferably the non-aqueous solvent is n-propanol By "stable pharmaceutical composition" is meant any pharmaceutical composition having sufficient stability to have utility as a pharmaceutical product. Preferably, a stable pharmaceutical composition has sufficient stability to allow storage at a convenient temperature, preferably between −20° C. and 40° C., more preferably about 2° C. to about 30° C., for a reasonable period of time, e.g., the shelf-life of the product which can be as short as one month but is typically six months or longer, more preferably one year or longer even more preferably twenty-four months or longer, and even more preferably thirty-six months or longer. The shelf-life or expiration can be that amount of time where the active ingredient degrades to a point below 90% purity. For purposes of the present description stable pharmaceutical composition includes reference to pharmaceutical compositions with specific ranges of impurities as described herein. Preferably, a stable pharmaceutical composition is one which has minimal degradation of the active ingredient, e.g., it retains at least about 85% of un-degraded active, preferably at least about 90%, and more preferably at least about 95%, after storage at 2-30° C. for a 2-3 year period of time.

By "stable dry-powder preparation" is meant any dry-powder preparation having sufficient stability, such characteristics as similarly defined herein for a stable pharmaceutical composition, to have utility as a pharmaceutical product.

By "degraded" is meant that the active has undergone a change in chemical structure, e.g., due to hydrolysis.

The term "therapeutically effective amount" as used herein refers to that amount of the compound being administered that will relieve to some extent one or more of the symptoms of the disorder being treated. In reference to the treatment of neoplasms, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer. Therapeutically effective amount can also mean preventing the disease from occurring in an animal that can be predisposed to the disease but does not yet experience or exhibit symptoms of the disease (prophylactic treatment). Further, therapeutically effective amount can be that amount that increases the life expectancy of a patient afflicted with a terminal disorder. Typical therapeutically effective doses for bendamustine for the treatment of non-Hodgkin's lymphoma can be from about 60-120 mg/$m^2$ given as a single dose on two consecutive days. The cycle can be repeated about every three to four weeks. For the treatment of chronic lymphocytic leukemia (CLL) bendamustine can be given at about 80-100 mg/$m^2$ on days 1 and 2. The cycle can be repeated after about 4 weeks. For the treatment of Hodgkin's disease (stages II-IV), bendamustine can be given in the "DBVBe regimen" with daunorubicin 25 mg/$m^2$ on days 1 and 15, bleomycin 10 mg/$m^2$ on days 1 and 15, vincristine 1.4 mg/$m^2$ on days 1 and 15, and bendamustine 50 mg/$m^2$ on days 1-5 with repetition of the cycle about every 4 weeks. For breast cancer, bendamustine (120 mg/$m^2$) on days 1 and 8 can be given in combination with methotrexate 40 mg/$m^2$ on days 1 and 8, and 5-fluorouracil 600 mg/$m^2$ on days 1 and 8 with repetition of the cycle about every 4 weeks. As a second-line of therapy for breast cancer, bendamustine can be given at about 100-150 mg/$m^2$ on days 1 and 2 with repetition of the cycle about every 4 weeks.

As used herein "neoplastic" refers to a neoplasm, which is an abnormal growth, such growth occurring because of a proliferation of cells not subject to the usual limitations of growth. As used herein, "anti-neoplastic agent" is any compound, composition, admixture, co-mixture, or blend which inhibits, eliminates, retards, or reverses the neoplastic phenotype of a cell.

As used herein "hyperproliferation" is the overproduction of cells in response to a particular growth factor. "Hyperproliferative disorders" are diseases in which the cells overproduce in response to a particular growth factor. Examples of such "hyperproliferative disorders" include diabetic retinopathy, psoriasis, endometriosis, cancer, macular degenerative disorders and benign growth disorders such as prostate enlargement.

As used herein, the term "vial" refers to any walled container, whether rigid or flexible.

"Controlling" as used herein means putting process controls in place to facilitate achievement of the thing being controlled. For example, in a given case, "controlling" can mean testing samples of each lot or a number of lots regularly or randomly; setting the concentration of degradants as a release specification; selecting process conditions, e.g., use of n-propanol or tert-butyl alcohol and/or other organic solvents in the pre-drying solution or dispersion, so as to assure that the concentration of degradants of the active ingredient is not unacceptably high; selecting a process concept, e.g., use of continuous drying, so as to assure that the concentration of degradants of the active ingredient is not unacceptably high; etc. Controlling for degradants by setting release specifications for the amount of degradants can be used to facilitate regulatory approval of a pharmaceutical product by a regulatory agency, such as the U.S. Food and Drug Administration and similar agencies in other countries or regions ("agency").

The term "pharmaceutically acceptable" as used herein means that the thing that is pharmaceutically acceptable, e.g., components, including containers, of a pharmaceutical composition, does not cause unacceptable loss of pharmacological activity or unacceptable adverse side effects. Examples of pharmaceutically acceptable components are provided in The United States Pharmacopeia (USP), The National Formulary (NF), adopted at the United States Pharmacopeial Convention, held in Rockville, Md. in 1990 and FDA Inactive Ingredient Guide 1990, 1996 issued by the U.S. Food and Drug Administration (both are hereby incorporated by reference herein, including any drawings). Other grades of solutions or components that meet necessary limits and/or specifications that are outside of the USP/NF can also be used.

The term "pharmaceutical composition" as used herein shall mean a composition that is made under conditions such that it is suitable for administration to humans, e.g., it is made under good manufacturing practice (GMP) conditions and contains pharmaceutically acceptable excipients, e.g., without limitation, stabilizers, bulking agents, buffers, carriers, diluents, vehicles, solubilizers, and binders. As used herein "pharmaceutical composition" includes, but is not limited to, a pre-drying solution(s) or dispersion(s) as well as a liquid form ready for injection or infusion after reconstitution of a dry-powder preparation.

A "pharmaceutical dosage form" as used herein means the pharmaceutical compositions disclosed herein being in a form of a tablet (usually referred to as single oral solid dosage form) or in a container and in an amount suitable for reconstitution and administration of one or more doses, typically about 1-2, 1-3, 1-4, 1-5, 1-6, 1-10, or about 1-20 doses. Preferably, a "pharmaceutical dosage form" as used herein means a dry-powder pharmaceutical composition disclosed herein in a container and in an amount suitable for reconstitution and delivery of one or more doses, typically about 1-2, 1-3, 1-4, 1-5, 1-6, 1-10, or about 1-20 doses. The pharmaceutical dosage form can comprise a vial or syringe or other suitable pharmaceutically acceptable container. The pharmaceutical dosage form suitable for injection or infusion use can include sterile aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The prevention of the growth of microorganisms can be accomplished by various antibacterial and antifungal agents, for example, parabens, chlorobutanol, phenol, sorbic acid, thimerosal, and the like.

"Pharmaceutically acceptable salt" refers to any salt of a compound provided herein which retains its biological properties and which is not toxic or otherwise undesirable for pharmaceutical use. Such salts can be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

As used herein, the term “excipient” means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term “excipient” encompasses carriers, diluents, vehicles, solubilizers, stabilizers, bulking agents, and binders. Excipients can also be those substances present in a pharmaceutical formulation as an indirect or unintended result of the manufacturing process. Preferably, excipients are approved for or considered to be safe for human and animal administration, e.g., generally regarded as safe (GRAS) substances. GRAS substances are listed by the Food and Drug administration in the Code of Federal Regulations (C.F.R.) at 21 C.F.R. § 182 and 21 C.F.R. § 184, incorporated herein by reference. Preferred excipients include, but are not limited to, hexitols, including mannitol and the like.

The term “aqueous excipient” refers to excipients, as defined above, that are soluble in aqueous solvents. In certain embodiments, an aqueous excipient is capable of partitioning into an aqueous solvent in preference to a non-aqueous solvent.

The term “non-aqueous excipient” refers to excipients, as defined above, that are soluble in non-aqueous solvents. In certain embodiments, a non-aqueous excipient is capable of partitioning into a non-aqueous solvent in preference to an aqueous solvent.

The term “organic solvent” means an organic material, usually a liquid, capable of dissolving other substances.

As used herein, “trace amount of an organic solvent” means an amount of solvent that is equal to or below recommended levels for pharmaceutical products, for example, as recommended by ICH guidelines (International Conferences on Harmonization, Impurities—Guidelines for Residual Solvents. Q3C. Federal Register. 1997; 62(247): 67377). The lower limit is the lowest amount that can be detected.

The term “release” or “at release” means the drug product has met the release specifications and can be used for its intended pharmaceutical purpose.

Compositions

Provided herein are solid dispersions of bendamustine and pharmaceutical compositions comprising the solid dispersions. The compositions can show greater stability and fewer impurities. In certain embodiments, the compositions comprise a limited amount of impurities. In certain embodiments, the compositions provide a limited amount of impurities after storage. It is believed that the increased stability of the compositions provided herein results from the limited aqueous exposure of the active components during manufacture and storage as well as the thermodynamic properties of the solid dispersions and the differences in the drying and solid state formation mechanisms between lyophilization and alternative forms of drying.

The compositions can be obtained from continuous drying of bendamustine, as described herein. In certain embodiments, a solid form is more easily reconstituted than the presently available lyophilized powder of bendamustine. Further, the compositions can provide a better impurity profile compared to Ribomustin® and/or Treanda® with respect to certain impurities, in particular HP1, bendamustine dimer, and bendamustine ethylester, prior to reconstitution, upon storage of the dry-powder, or following reconstitution and admixture.

Because of its instability in aqueous solutions due to hydrolysis with water, bendamustine requires drying into a dry powder in order to make a product suitable for pharmaceutical use. During the manufacturing of lyophilized drug products, aqueous solutions are commonly needed for filling, prior to lyophilization. Thus, the use of aqueous solutions during compounding and fill processes for lyophilized bendamustine and other nitrogen mustards can result in degradation of the drug product. Continuous spray drying, as described herein, provides for very short contact times between bendamustine and water, thus inhibiting the creation of degradation products. Additionally, spray drying provides uniform dry-powder particles which provide enhanced reconstitution properties due to the increased surface area of the dry powder.

The compositions comprise bendamustine or a pharmaceutically acceptable salt thereof. Bendamustine is 4-{5-[bis(2-chloroethyl)amino]-1-methyl-2-benzimidazolyl}butyric acid, depicted as an HCl salt in Formula I:

Formula I

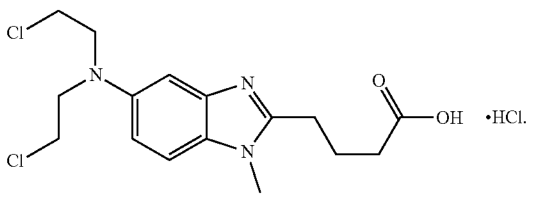

Bendamustine can be in any chemical form known to those of skill in the art. In certain embodiments, the bendamustine is a pharmaceutically acceptable salt of bendamustine. In particular embodiments, the bendamustine is an HCl salt of bendamustine, as depicted in Formula I.

The bendamustine can be crystalline or amorphous, or a mixture of crystalline and amorphous bendamustine. In certain embodiments, the bendamustine is crystalline. Crystalline bendamustine can be in any crystalline form known to those of skill in the art, or a mixture of crystalline forms. In particular embodiments, the bendamustine is amorphous.

In advantageous embodiments, the bendamustine is in a solid form. In particular embodiments, the bendamustine is in the form of a solid dispersion. The solid form can be a dried solid dispersion, fluidized bed spray-dried solid dispersion, or a granulation solid dispersion. In certain embodiments, the solid form is a hot melt extrusion solid dispersion. In certain embodiments, the solid form is a lyophilisation solid dispersion. Techniques for preparing the solid forms are described in detail herein.

The solid dispersions can show greater stability and fewer impurities. In certain embodiments, the solid dispersions comprise a limited amount of impurities. In certain embodiments, the solid dispersions provide a limited amount of impurities after storage. The solid dispersions can be components of the pharmaceutical compositions. The solid dispersions can have each of the characteristics described herein for the pharmaceutical compositions. For instance, in certain embodiments, the solid dispersions comprise the forms of bendamustine, little or no water, the non-aqueous solvent and/or the pharmaceutically acceptable carriers, excipients or diluents as described herein. In certain embodiments, any pharmaceutical composition can comprise, outside the bendamustine solid dispersions, little or no water, non-aqueous solvent, and any pharmaceutically acceptable carriers, excipients or diluents, or combinations thereof, in addition to within the solid dispersions. In certain embodiments, solid dispersions comprise 90% particles less than 50 μm in diameter. In certain embodiments, solid dispersions comprise 90% particles between 20 μm and 50 μm in diameter. In certain embodiments, the morphology and physical characteristics of the powder particles enable consistent powder flow.

In particular embodiments, provided herein are pharmaceutical compositions comprising the solid forms along with one or more pharmaceutically acceptable carriers, excipients or diluents. Advantageously, the pharmaceutical compositions of bendamustine can show remarkable stability or remarkable purity, or both. It is believed that the pharmaceutical compositions of bendamustine, as described herein, comprise little or no water, thereby preventing aqueous degradation of the bendamustine.

In certain embodiments, the solid forms or pharmaceutical compositions comprise little or no water. In certain embodiments, the solid forms or pharmaceutical compositions comprise substantially no water. In certain embodiments, the solid forms or pharmaceutical compositions comprise less than 1%, less than 0.75%, less than 0.5%, less than 0.25%, or less than 0.1% by weight water.

In certain embodiments, the solid forms or pharmaceutical compositions comprise a non-aqueous solvent. As described herein, the non-aqueous solvent can facilitate preparation of the compositions. In certain embodiments, the solid forms or pharmaceutical compositions comprise a trace amount of a non-aqueous solvent. In certain embodiments, the solid forms or pharmaceutical compositions comprise less than 1%, less than 0.75%, less than 0.5%, less than 0.25%, or less than 0.1% by weight non-aqueous solvent.

In certain embodiments, the non-aqueous solvent is selected from the group consisting of tert-butanol, n-propanol, n-butanol, isopropanol, ethanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, N-methyl-2-pyrrolidone (NMP), dimethyl formamide (DMF), dimethyl acetamide (DMA), acetic acid, and cyclohexane, and mixtures thereof. Preferred organic solvents include one or more of ethanol, methanol, dichloromethane, dimethyl sulfoxide, propanol, butanol, isopropanol, N-methyl-2-pyrrolidone (NMP), dimethyl formamide (DMF), dimethyl acetamide (DMA) and tert-butanol, and mixtures thereof. In certain embodiments, the non-aqueous solvent is selected from the group consisting of tert-butanol, n-propanol, n-butanol, isopropanol, ethanol, methanol, acetone, ethyl acetate, dimethyl carbonate, acetonitrile, dichloromethane, methyl ethyl ketone, methyl isobutyl ketone, 1-pentanol, methyl acetate, carbon tetrachloride, dimethyl sulfoxide, hexafluoroacetone, chlorobutanol, dimethyl sulfone, acetic acid, cyclohexane, and mixtures thereof. In certain embodiments, the non-aqueous solvent is selected from the group consisting of ethanol, methanol, propanol, butanol, isopropanol, tert-butanol, and mixtures thereof.

The solid forms or pharmaceutical compositions can further comprise one or more pharmaceutically acceptable carriers, excipients or diluents. In certain embodiments, the carriers, excipients, or diluents can be any deemed useful to the practitioner of skill. Exemplary carriers, excipients and diluents are described herein.

In certain embodiments, the solid forms or pharmaceutical compositions comprise a polymer excipient. In particular embodiments, the polymer excipient is capable of being dissolved in a non-aqueous solvent. In certain embodiments, the polymer excipient is a polymer of vinylpyrrolidone, hydroxypropyl methyl cellulose, hydroxypropyl methyl cellulose acetate succinate (HPMC-AS), ethylene glycol, propylene glycol, propylene carbonate, vinyl acetate, vinyl propionate, vinyl caprolactam, cellulose acetate, ethyl cellulose, methyl methacrylate, methacrylic acid, or combinations thereof.

In certain embodiments, the solid forms or pharmaceutical compositions comprise a saccharide excipient or saccharide alcohol excipient. A pharmaceutically acceptable spray drying excipient can be dissolved in an aqueous solution. In certain embodiments, the excipient is selected from the group consisting of mannitol, maltitol, sorbitol, erythritol, xylitol, lactitol, lactose, sucrose, glycose, maltose, trehalose, dextrose, and combinations thereof. In certain embodiments, the excipient is mannitol.

In certain embodiments, the weight ratio of bendamustine to excipient is between about 5:1 and about 1:20 bendamustine to excipient. In certain embodiments, the weight ratio of bendamustine to excipient is about 1:1.7 bendamustine to excipient The compositions provided herein can have remarkable purity and remarkable stability. Generally, stability is evaluated by measuring the amount of impurities in the composition. In particular embodiments, stability is evaluated by measuring the amount of impurities provided by the composition following storage for a period of time. The composition can be evaluated at the time of manufacture or at a time after manufacture. In certain embodiments, a composition is evaluated at time zero, i.e. at the time of release. In certain embodiments, a composition is evaluated after manufacture at one month, two months, three months, six months, nine months, twelve months, eighteen months, twenty-four months and/or thirty-six months. Storage can be at any temperature deemed suitable to the practitioner of skill. In certain embodiments, storage is between −20° C. and 25° C. In certain embodiments, storage is at about 2° C. to about 30° C. In certain embodiments, the composition is stored at 25° C., 5° C., −5° C., or −20° C. Preferred temperatures for storage are about 5° C. and about room temperature. Components of the compositions can be determined by standard techniques, such as those described in the examples. In exemplary embodiments, components are evaluated by dissolution in a non-aqueous solvent followed by high performance liquid chromatography.

Because of their purity and stability, the compositions provided herein comprise limited amounts of bendamustine degradation products. Bendamustine degradation products include HP1, bendamustine dimer, bendamustine ethyl ester (BM1EE), des-chloroethyl bendamustine (BM1DCE), HP2, and combinations and multimers thereof.

The term "HP1" refers to a compound of formula II:

Formula II

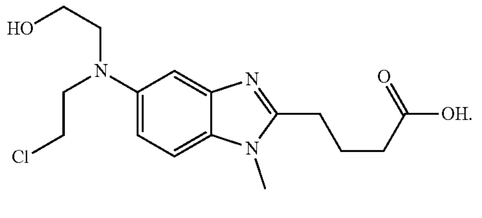

The term "bendamustine dimer" refers to a compound of Formula III:

Formula III

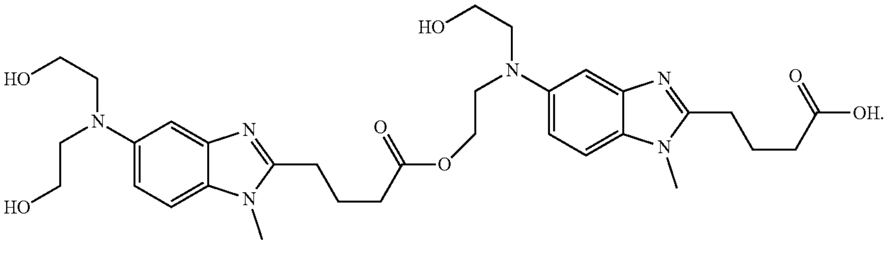

The terms "bendamustine ethyl ester" and "BM1EE" refer to a compound of Formula IV:

Formula IV

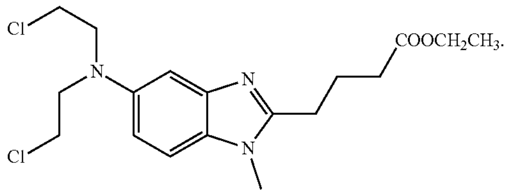

The terms "des-chloroethyl bendamustine" and "BM1DCE" refer to a compound of Formula V:

Formula V

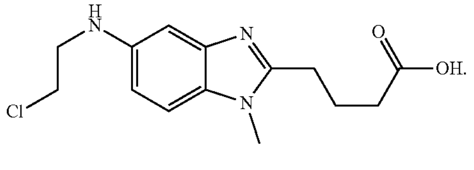

The term "HP2" refers to a compound of Formula VI.

Formula VI

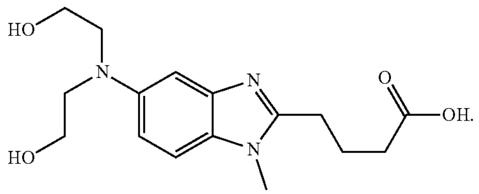

In certain embodiments, the compositions provided herein provide little or no bendamustine degradation products. In certain embodiments, the degradation products are measured at the time of release, i.e. time zero, or at two months, six months, twelve months, eighteen months, twenty-four months or thirty-six months after release. The bendamustine degradation products can be measured by any technique deemed suitable by one of skill. The compositions can be evaluated, for instance, by dissolution in a non-aqueous solvent such as methanol. Useful measurement techniques include gas chromatography, mass spectrometry and high performance liquid chromatography (HPLC). The bendamustine degradation products are evaluated relative to the amount of bendamustine in the composition. For instance, an amount of a bendamustine degradation product can be measured by HPLC as area percent of the degradation product relative to the bendamustine area on an HPLC trace (i.e., area percent bendamustine). For measurement of degradation products, the composition is stored at a temperature deemed acceptable by the practitioner according to accepted practice. In certain embodiments, the composition is between −20° C. and 25° C. In certain embodiments, the composition is stored at 25° C., 5° C., −5° C., or −20° C.

In certain embodiments, the composition provides less than 3.9% total bendamustine degradation products, relative to bendamustine. In certain embodiments, the composition provides less than 3.5% total bendamustine degradation products, relative to bendamustine. In certain embodiments, the composition provides less than 2.0% to 3.9% total bendamustine degradation products, relative to bendamustine.

In certain embodiments, the composition provides less than 0.4% to about 0.8% HP1, relative to bendamustine. In certain embodiments, the composition provides less than 0.5%, 0.4%, 0.3%, 0.2%, 0.15%, or 0.1% HP1, relative to bendamustine. In certain embodiments, the composition provides less than 0.5% HP1, relative to bendamustine. In certain embodiments, the composition provides less than 0.4% HP1, relative to bendamustine. In certain embodiments, the composition provides less than 0.3% HP1, relative to bendamustine. In certain embodiments, the composition provides less than 0.2% HP1, relative to bendamustine. In certain embodiments, the composition provides less than 0.15% HP1, relative to bendamustine. In certain embodiments, the composition provides less than 0.1% HP1, relative to bendamustine.

In certain embodiments, the composition provides less than 0.4% to about 0.8% bendamustine dimer, relative to bendamustine. In certain embodiments, the composition provides less than 0.5%, 0.4%, 0.3%, 0.2%, 0.15%, or 0.1% bendamustine dimer, relative to bendamustine. In certain embodiments, the composition provides less than 0.5% bendamustine dimer, relative to bendamustine. In certain embodiments, the composition provides less than 0.4% bendamustine dimer, relative to bendamustine. In certain embodiments, the composition provides less than 0.3% bendamustine dimer, relative to bendamustine. In certain embodiments, the composition provides less than 0.2% bendamustine dimer, relative to bendamustine. In certain embodiments, the composition provides less than 0.15% bendamustine dimer, relative to bendamustine. In certain embodiments, the composition provides less than 0.1% bendamustine dimer, relative to bendamustine.

In certain embodiments, the composition provides less than 0.4% to about 0.8% BM1EE, relative to bendamustine. In certain embodiments, the composition provides less than 0.5%, 0.4%, 0.3%, 0.2%, 0.15%, or 0.1% BM1EE, relative to bendamustine. In certain embodiments, the composition provides less than 0.5% BM1EE, relative to bendamustine. In certain embodiments, the composition provides less than 0.4% BM1EE, relative to bendamustine. In certain embodiments, the composition provides less than 0.3% BM1EE, relative to bendamustine. In certain embodiments, the composition provides less than 0.2% BM1EE, relative to bendamustine. In certain embodiments, the composition provides less than 0.15% BM1EE, relative to bendamustine. In certain embodiments, the composition provides less than 0.1% BM1EE, relative to bendamustine.

In certain embodiments, the composition provides less than 0.4% to about 0.8% BM1DCE, relative to bendamustine. In certain embodiments, the composition provides less than 0.5%, 0.4%, 0.3%, 0.2%, 0.15%, or 0.1% BM1DCE, relative to bendamustine. In certain embodiments, the composition provides less than 0.5% BM1DCE, relative to bendamustine. In certain embodiments, the composition provides less than 0.4% BM1DCE, relative to bendamustine. In certain embodiments, the composition provides less than 0.3% BM1DCE, relative to bendamustine. In certain embodiments, the composition provides less than 0.2% BM1DCE, relative to bendamustine. In certain embodiments, the composition provides less than 0.15% BM1DCE, relative to bendamustine. In certain embodiments, the composition provides less than 0.1% BM1DCE, relative to bendamustine.

In certain embodiments, the composition provides less than 0.4% to about 0.8% HP2, relative to bendamustine. In certain embodiments, the composition provides less than 0.5%, 0.4%, 0.3%, 0.2%, 0.15%, or 0.1% HP2, relative to bendamustine. In certain embodiments, the composition provides less than 0.5% HP2, relative to bendamustine. In certain embodiments, the composition provides less than 0.4% HP2, relative to bendamustine. In certain embodiments, the composition provides less than 0.3% HP2, relative to bendamustine. In certain embodiments, the composition provides less than 0.2% HP2, relative to bendamustine. In certain embodiments, the composition provides less than 0.15% HP2, relative to bendamustine. In certain embodiments, the composition provides less than 0.1% HP2, relative to bendamustine.

In certain embodiments, the composition provides less than 2.0% to about 3.9% total HP1, bendamustine dimer, BM1EE, BM1DCE and HP2, relative to bendamustine. In certain embodiments, the composition provides less than 0.5%, 0.4%, 0.3%, 0.2%, 0.15%, or 0.1% total HP1, bendamustine dimer, BM1EE, BM1DCE and HP2, relative to bendamustine. In certain embodiments, the composition provides less than 3.9% total HP1, bendamustine dimer, BM1EE, BM1DCE and HP2, relative to bendamustine. In certain embodiments, the composition provides less than 3.5% total HP1, bendamustine dimer, BM1EE, BM1DCE and HP2, relative to bendamustine.

In further embodiments, provided herein are pharmaceutical dosage forms comprising one or more of the pharmaceutical compositions or solid dispersions described herein. The pharmaceutical dosage form can comprise an amount of active bendamustine to provide a single dose or multiple doses of the active bendamustine to a patient in need thereof. In certain embodiments, the dosage form can be about 5 to about 500 mg of bendamustine, about 10 to about 300 mg of bendamustine, about 25 mg of bendamustine, about 100 mg of bendamustine, or about 200 mg of bendamustine. In particular embodiments, the dosage forms have the purity and/or stability described herein. In further embodiments, the pharmaceutical dosage forms comprise integer multiples of one of the above amounts. In certain embodiments, the dosage form can be reconstituted into a pharmaceutically acceptable injectable form within 5, 4, 3, 2, or 1 minutes. In certain embodiments, the dosage form is an oral dosage form.

In certain embodiments, provided herein is a pharmaceutical product having a release specification for bendamustine degradants. The release specification is at the amounts described herein. In certain embodiments, provided herein is a pharmaceutical product having a release specification for total bendamustine degradants at less than about 3.9%, preferably about 2.0% to about 3.9%. In certain embodiments, provided herein is a pharmaceutical product having a release specification for total HP1, bendamustine dimer, BM1EE, BM1DCE and HP2, less than 3.9%, relative to bendamustine. In certain embodiments, provided herein is a pharmaceutical product having a release specification for total HP1, bendamustine dimer, BM1EE, BM1DCE and HP2, at less than 2.0% to 3.9%, relative to bendamustine. In certain embodiments, provided herein is a pharmaceutical product having a shelf-life specification for bendamustine degradants at less than about 6.9%, preferably about 5.0% to about 6.9%, relative to bendamustine, where the product is stored at about 2° C. to about 30° C. In certain embodiments, provided herein is a pharmaceutical product having a shelf-life specification for total HP1, bendamustine dimer, BM1EE, BM1DCE and HP2 at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein is a pharmaceutical product having a release specification for HP1 at less than 0.4% to about 0.8%, relative to bendamustine. In certain embodiments, provided herein is a pharmaceutical product having a release specification for HP1 at less than 0.5%, 0.4%, 0.3%, 0.2%, 0.15%, or 0.1%, relative to bendamustine. In certain embodiments, provided herein is a pharmaceutical product having a shelf-life specification for HP1 at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein is a pharmaceutical product having a release specification for bendamustine dimer at less than 0.4% to about 0.8%, relative to bendamustine. In certain embodiments, provided herein is a pharmaceutical product having a release specification for bendamustine dimer at less than 0.5%, 0.4%, 0.3%, 0.2%, 0.15%, or 0.1%, relative to bendamustine. In certain embodiments, provided herein is a pharmaceutical product having a shelf-life specification for bendamustine dimer at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein is a pharmaceutical product having a release specification for BM1EE at less than 0.4% to about 0.8%, relative to bendamustine. In certain embodiments, provided herein is a pharmaceutical product having a release specification for BM1EE at less than 0.5%, 0.4%, 0.3%, 0.2%, 0.15%, or 0.1%, relative to bendamustine. In certain embodiments, provided herein is a pharmaceutical product having a shelf-life specification for BM1EE at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein is a pharmaceutical product having a release specification for BM1DCE at less than 0.4% to about 0.8%, relative to bendamustine. In certain embodiments, provided herein is a pharmaceutical product having a release specification for BM1DCE at less than 0.5%, 0.4%, 0.3%, 0.2%, 0.15%, or 0.1%, relative to bendamustine. In certain embodiments, provided herein is a pharmaceutical product having a shelf-life specification for BM1DCE at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein is a pharmaceutical product having a release specification for HP2 at less than 0.4% to about 0.8%, relative to bendamustine. In certain embodiments, provided herein is a pharmaceutical product having a release specification for HP2 at less than 0.5%, 0.4%, 0.3%, 0.2%, 0.15%, or 0.1%, relative to bendamustine. In certain embodiments, provided herein is a pharmaceutical product having a shelf-life specification for HP2 at less than about 6.9%, preferably about 5.0% to about 6.9%, relative to bendamustine, where the product is stored at about 2° C. to about 30° C. In certain embodiments, the product is stored at 25° C., 5° C., −5° C., or −20° C.

In certain embodiments, provided herein are methods for obtaining agency approval for a bendamustine product as described herein. In these embodiments, the product meets one or more of the specifications described herein. These methods generally comprise the step of seeking agency approval for a pharmaceutical product having one or more of the release specifications described herein.

Methods of Manufacture

Also provided herein are methods of making the bendamustine solid dispersions and pharmaceutical compositions. The methods generally comprise manufacture of a bendamustine composition while controlling for the amounts of bendamustine degradation products as described herein and controlling the solid state thermodynamic properties of the ensuing solid dispersion. Further provided are formulations useful in the methods.

In certain embodiments, a process for manufacturing a solid dispersion of bendamustine is provided which includes controlling for the concentration of bendamustine degradants in the final product, such that the concentration of bendamustine degradants is less than about 3.9%, or is less than about 3.5%, preferably no more than about 2.0% to about 3.9%, (area percent of bendamustine) at release or otherwise to achieve the pharmaceutical compositions described herein. In certain embodiments, the bendamustine product herein contains not more than about 0.4% to about 0.8%, preferably about 0.4%, (area percent of bendamustine) HP1 at release.

In certain embodiments, provided is a process for manufacturing a solid dispersion of bendamustine which comprises controlling for the concentration of bendamustine degradants in the final product, such that, at release, the concentration of HP1 is less than 0.8%, preferably 0.4%, (area percent of bendamustine) and, at the time of product expiration, the concentration of bendamustine degradants is less than about 6.9%, preferably no more than about 5.0% to about 6.9%; wherein the product is stored at about 2° C. to about 30° C.

As described herein, a solid dispersion of bendamustine can be achieved following removal of an organic solvent. A useful solvent for preparing a solid dispersion is tert-butanol. Other organic solvents can be used including ethanol, n-propanol, n-butanol, isopropanol, ethyl acetate, dimethyl carbonate, acetonitrile, dichloromethane, methyl ethyl ketone, methyl isobutyl ketone, 1-pentanol, methyl acetate, methanol, carbon tetrachloride, dimethyl sulfoxide, dimethyl acetamide, hexafluoroacetone, chlorobutanol, dimethyl sulfone, acetic acid, cyclohexane, N-methyl-2-pyrrolidone, and dimethylformamide. These preceding solvents can be used individually or in combination. Useful solvents should form stable solutions with bendamustine and must not appreciably degrade or deactivate the bendamustine. The solubility of bendamustine in the selected solvent should be high enough to form commercially useful concentrations of the drug in solvent. Additionally, the solvent should be capable of being removed easily from an aqueous dispersion or solution of the bendamustine, e.g., through spray drying. In certain embodiments, a solution having a concentration of about 0.25 to 300 mg/mL, 0.25 to 200 mg/mL, 2-80 mg/mL, preferably about 5 to 40 mg/mL, more preferably 5-20 mg/mL and even more preferably 12 to 17 mg/mL bendamustine is useful.

A pharmaceutically acceptable spray drying excipient can be dissolved in an aqueous solution. Examples of useful excipients include, without limitation, sodium or potassium phosphate, citric acid, tartaric acid, gelatin, glycine, and carbohydrates such as lactose, sucrose, maltose, glycerin, dextrose, dextran, trehalose and hetastarch. Mannitol is a preferred excipient. Other excipients that can be used if desired include antioxidants, such as, without limitation, ascorbic acid, acetylcysteine, cysteine, sodium hydrogen sulfite, butyl-hydroxyanisole, butyl-hydroxytoluene or alpha-tocopherol acetate, and chelators. In certain embodiments, the excipient is selected from the group consisting of mannitol, maltitol, sorbitol, erythritol, xylitol, lactitol, lactose, sucrose, glycose, maltose, trehalose, dextrose, and combinations thereof.

An exemplary formulation and spray-drying run is provided herein. Spray drying can be carried out using standard equipment as used for spray drying. The drying run can be varied depending upon the equipment and facilities used for the fill/finish.

Figure 4:
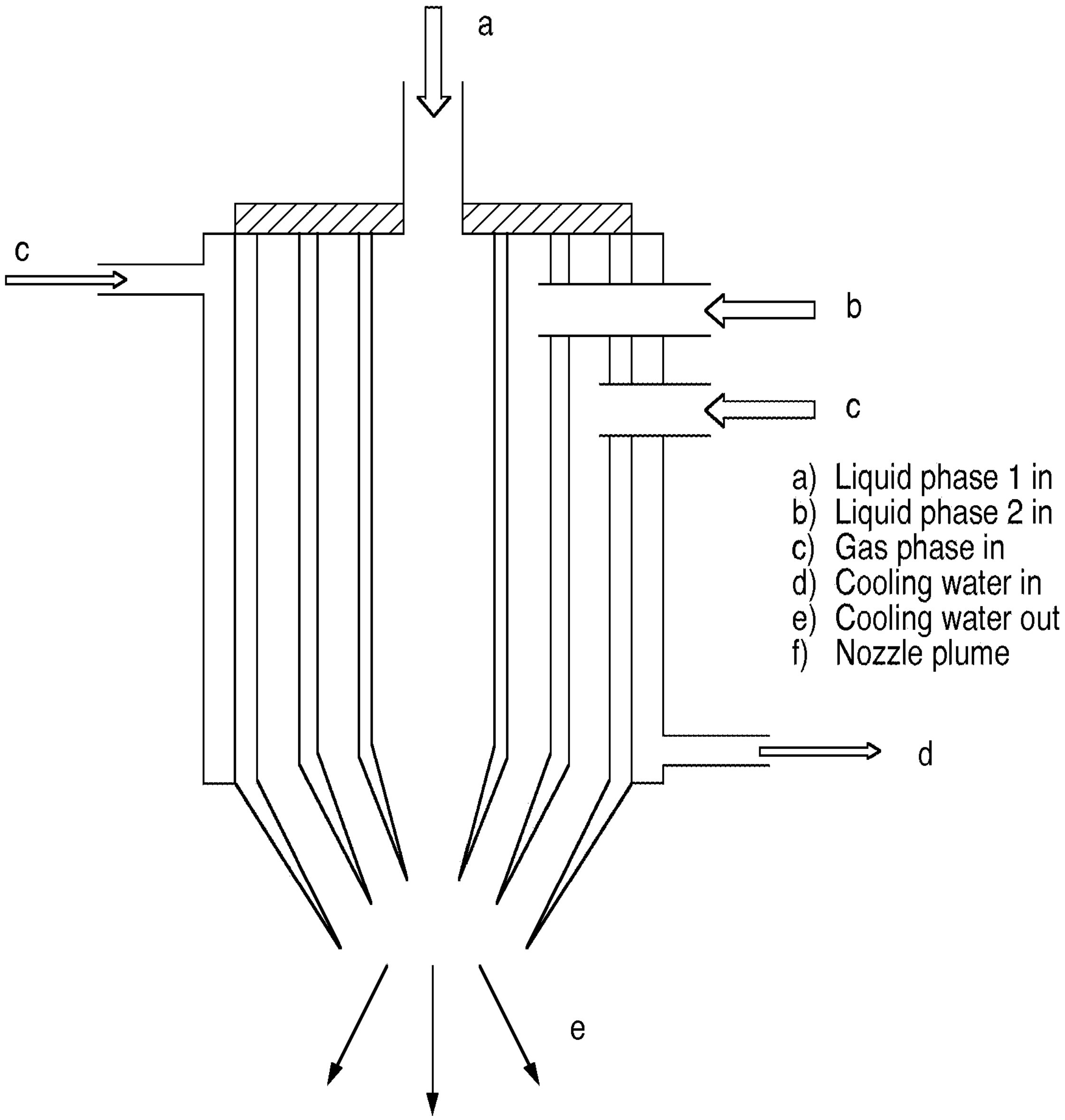
FIG. 4 provides a detailed view of a 2-liquid-phase spray nozzle useful for producing bendamustine dry-powder.

In accordance with a typical embodiment, a non-aqueous pre-drying solution or dispersion comprising bendamustine is first formulated in a pharmaceutically acceptable compounding vessel. An aqueous pre-drying solution or dispersion containing an acceptable excipient is also formulated in a separate pharmaceutically acceptable compounding vessel. Both solutions are then aseptically filtered, mixed by means of an in-line static mixer and continuously fed into the spray drier. In an embodiment, the aqueous and non-aqueous solutions comprise the two liquid inputs in a two-liquid-phase nozzle of a spray drier (see FIGS. 3 and 4). Using spray drying techniques described herein the solutions are spray-dried until a moisture content in the range of about 0.01 to about 8.0 percent is achieved. To obtain such moisture levels, secondary drying may be used. The resulting dry-powder can be stable for about six months to greater than about 2 years, preferably greater than about 3 years at about 5° C. to about 25° C. The dry-powder can be readily reconstituted with Sterile Water for Injection, or other suitable carrier, to provide liquid formulations of bendamustine, suitable for internal administration, e.g., by parenteral injection. For intravenous administration, the reconstituted liquid formulation, e.g., the pharmaceutical composition is preferably a solution.

The pre-drying aqueous solution or dispersion normally is first formulated in a pharmaceutically acceptable container by: 1) adding an excipient, such as mannitol (about 10 to about 50 mg/mL) with mixing to water (about 65% of the total volume) at ambient temperature. The pre-drying non-aqueous solution or dispersion is formulated in a pharmaceutically acceptable container by: 1) adding bendamustine HCl to the desired concentration with mixing, 2) cooling the solution to about 1° C. to about 30° C., preferably about 5° C. Although the preceding steps are provided in a certain order, it is understood that one skilled in the art can change the order of the steps and quantities as needed. Quantities can be prepared on a weight basis also.

The pre-drying aqueous and pre-drying non-aqueous solutions or dispersions can be sterilized prior to spray drying. Sterilization is generally performed by aseptic filtration, e.g., through a 0.22 micron or less filter. Multiple sterilization filters can be used. Sterilization of the solution or dispersion can be achieved by other methods known in the art, e.g., radiation.

After sterilization, both solutions and dispersions are ready for spray drying. In certain embodiments, the filtered solutions are introduced into the spray drier in a continuous mode of operation. The formulation can be effectively and efficiently spray-dried in collection containers. Advantageously, the product can be aseptically filled into the containers which the product is to be marketed in, such as, without limitation, a vial, as described herein and as known in the art.

To assure sterility, the collection containers can undergo terminal sterilization before filling the product into the containers which the product is to be marketed in, such as, without limitation, a vial. Terminal sterilization can be achieved by methods known in the art, e.g., radiation.

An exemplary procedure for use in spray drying the pre-drying solutions or dispersions is set forth below. However, a person skilled in the art would understand that modifications to the procedure or process can be made depending on such things as, but not limited to, the pre-drying solution or dispersion and spray drying equipment.

Initially, the air flow of the spray drier is set to the desired operating rate. This rate depends on the desired quantity to be spray dried, the desired pressure drop across the spray drying system and the geometry and size of the spray drying apparatus and can be calculated by heat and energy balances as known in the art. The air will be heated by means of a heat exchanger. The heat duty of the heat exchanger is adjusted appropriately so as to obtain a targeted temperature at the outlet of the spray chamber. A useful range for this temperature is between about 50° C. and about 120° C. A further useful temperature is between about 60° C. and about 90° C. A particularly useful temperature is between about 70° C. and about 80° C. In certain embodiments, inert gas of high enthalpy, such as nitrogen, can be used. In certain embodiments, air or inert gas of high enthalpy is at about 0.5 to about 0.99 atmosphere pressure. In certain embodiments, air or inert gas of high enthalpy is less than about 0.99 atmosphere pressure. In certain embodiments, air or inert gas of high enthalpy is about 0.5 to about 1.5 atmosphere pressure.

Next, the atomizer air-flow rate into the spray nozzle of the spray drier is set to a desired operating value. This flow rate depends on the kind and geometry of the nozzle and the desired properties of the resulting dry-powder particles.

The feeding rate of the aqueous pre-drying solution is then ramped up to the desired flow rate. The feeding rate is adjusted appropriately so as to obtain a targeted temperature at the outlet of the spray chamber. A useful range for this temperature is between about 50° C. and about 120° C. A further useful temperature is between about 60° C. and about 90° C. A particularly useful temperature is between about 70° C. and about 80° C.

The feeding rate of the non-aqueous pre-drying solution is then ramped up to the desired flow rate. The feeding rate is adjusted appropriately so as to obtain a desired ratio of bendamustine to mannitol and maintain a targeted temperature at the outlet of the spray chamber. In certain embodiments, the ratio of bendamustine to excipient is between 5:1 and 1:20. A preferred weight ratio of mannitol to bendamustine is between about 1 to about 5. An even more preferred weight ratio of mannitol to bendamustine is between about 1.2 to about 3. An even more preferred weight ratio of mannitol to bendamustine is between about 1.5 to about 2. An even more preferred weight ratio of mannitol to bendamustine is about 1.7. A useful range for this temperature is between about 50° C. and about 120° C. A further useful temperature is between about 60° C. and about 90° C. A particularly useful temperature is between about 70° C. and about 80° C.

While the system is in transient operating conditions, the resulting dry-powder is collected into appropriate containers at the outlet of the powder collection system. The dry powder collected during this phase is not the desired product. Once the system reaches steady-state, the collection containers are changed to appropriate pharmaceutical containers acting as collection containers. The dry powder that is now collected is the desired dry-powder bendamustine composition.

Once the desired quantity of dry-powder bendamustine is produced, the collection container is switched again and the system is ramped down in the reverse order. The dry powder collected during this phase is not the desired product.

After spray drying, the bendamustine dry-powder can be filled into containers, such as vials. Typically an aseptic powder-filling machine can be used, as known in the art. Typically, a vial will contain a dry-powder including about 10-500 mg/vial, preferably about 100 mg/vial, bendamustine and about 5 mg-2 g/vial, preferably about 170 mg/vial, mannitol. Several representative samples can be removed for purposes of performing various physical, chemical, and microbiological tests to analyze the quality of the product.

In further embodiments, provided herein are formulations useful for preparing the compositions described herein. In certain embodiments, provided is a bendamustine pre-drying solution or dispersion comprising one or more organic solvents where the solution or dispersions include at least one concentration of an organic solvent which reduces the level of degradation of bendamustine so that the amount of HP1 produced during continuous drying from about 0 to 24 hours does not exceed about 0.4% to about 0.8% (area percent of bendamustine) preferably 0.40%, preferably 0.35%, more preferably 0.30%, more preferably 0.25%, even more preferably 0.20%. An aspect of this embodiment is the dry powder produced from the pre-drying solution or dispersion.

Still another embodiment is a bendamustine pre-drying solution or dispersion comprising one or more organic solvents where the solution or dispersions include at least one concentration of an organic solvent which reduces the level of degradation of bendamustine so that the amount of bendamustine ethylester produced during continuous drying from about 0 to 24 hours does not exceed about 0.5% (area percent bendamustine). An aspect of this embodiment is the dry powder produced from the pre-drying solution or dispersion.

Still another embodiment is a bendamustine pre-drying solution or dispersion comprising one or more organic solvents where the solution or dispersions include at least one concentration of an organic solvent which reduces the level of degradation of bendamustine so that the amount of bendamustine ethylester (Formula IV) produced during continuous drying from about 0 to 24 hours is no more than 0.2%, preferably 0.1%, greater than the concentration of bendamustine ethylester as found in the drug substance used to make the pre-drying solution. Preferred organic solvents are methylene chloride, dimethyl sulfoxide, acetonitrile, acetone, N-methyl-2-pyrrolidone (NMP), dimethyl formamide (DMF), dimethyl acetamide (DMA), n-propanol and tert-butanol.

In further embodiments, provided herein are methods for preparing a bendamustine dry-powder preparation from a non-aqueous solvent. The methods comprise the steps of dissolving bendamustine in a concentration of an organic solvent of between about 5% to about 100% (v/v organic solvent to form a pre-drying solution); and continuously drying the pre-drying solution. In certain embodiments, the resulting bendamustine dry-powder preparation made from such methods comprises not more than about 0.4% to about 0.8%, preferably 0.4%, (area percent of bendamustine) HP1. In certain embodiments, the HP1 is the amount of HP1 present at release or at time zero after reconstitution of the dry-powder pharmaceutical composition of bendamustine. Useful concentrations of the organic solvent are from about 90% to about 100%. Useful organic solvents include one or more of methanol, ethanol, propanol, iso-propanol, butanol, acetone, acetonitrile, dimethyl sulfoxide, methylene chloride, N-methyl-2-pyrrolidone (NMP), dimethyl formamide (DMF), dimethyl acetamide (DMA) and tert butanol. In particular embodiments, the organic solvent is selected from acetone, acetonitrile, dimethyl sulfoxide, methylene chloride, N-methyl-2-pyrrolidone (NMP), dimethyl formamide (DMF), dimethyl acetamide (DMA), tert-butanol, and mixtures thereof. A useful concentration of acetone, acetonitrile, dimethyl sulfoxide, methylene chloride, N-methyl-2-pyrrolidone (NMP), dimethyl formamide (DMF), dimethyl acetamide (DMA) and tert-butanol is from about 40% to about 100%. Useful pre-drying concentrations of bendamustine are from about 2 mg/mL to about 300 mg/mL. Particularly useful pre-drying concentrations of bendamustine are from about 10 mg/mL to about 150 mg/mL.

In certain embodiments, an excipient is added before continuous drying. A preferred excipient is mannitol, lactose or sucrose. A more preferred excipient is mannitol. However, mannitol cannot be dissolved in completely organic solvent systems. Therefore, mannitol is typically first dissolved in water.

In certain embodiments, an aqueous solution of mannitol is combined with a pre-drying solution of bendamustine immediately before continuous drying. Because of the relatively short contact time between bendamustine and water, the amount of HP1 degradation product is significantly reduced compared to existing methods. The combination of the pre-drying solution of bendamustine with the aqueous solution of the excipient will be done before entry to the main chamber of the continuous drier. Complete mixing of the two solutions can be achieved by means of a continuous mixing device. A useful continuous mixing device is an in-line static mixer. A useful continuous combination system is a hot melt extruder. A useful continuous drying system is a spray drying system or a fluidized bed drying system. A particularly useful continuous drying system is a spray drying system.

In further embodiments, provided is a drying method where the pre-drying bendamustine solution is combined with the excipient aqueous solution in a two-liquid-flow nozzle inside the spray-drying chamber.

In a useful method for preparing a bendamustine dry-powder preparation, spray drying the pre-drying solution comprises: i) setting the spray drier air flow temperature at an operating temperature between about 40° C. to about 120° C.; ii) adjusting the spray drier air flow to an appropriate rate depending on the desired flow rate of the pre-drying solution and calculated by the appropriate mass and energy balance; iii) adjusting the spray drier atomizer air flow to an appropriate rate depending on the desired dry-particle properties; iv) ramping up the flow rate of the pre-drying solution into the spray drier to a value appropriate to the size of the spray drying system; v) adjusting the flow rate into the spray drier of the aqueous solutions which contains the excipient to a rate calculated by appropriate mass balances so as to obtain the desired weight ratio of bendamustine to excipient in the final dry-powder; vi) collecting the dry-powder produced during the ramp up operation into a separate container; vii) switching to another container once steady state conditions have been obtained (this container contains the desired dry-powder); viii) operating the spray drier continuously for a sufficient period of time so as to obtain the desired quantity of the bendamustine dry-powder; and ix) switching to a ramp-down powder collecting container once the desired quantity has been produced. A useful formulation includes bendamustine at a concentration of about 15 mg/mL and mannitol at a concentration of about 25.5 mg/mL.

In certain embodiments, provided herein is a dry-powder prepared according to any of the methods described herein.

In certain embodiments, also provided are bendamustine formulations for spray drying that include an excipient and a concentration of an organic solvent. In certain embodiments, provided is a set of formulations for continuous drying comprising bendamustine in a non-aqueous solvent at a concentration between 0.25 mg/ml to 300 mg/ml and mannitol in water at a concentration between 0.25 mg/ml to 500 mg/ml. A preferred set of formulations includes bendamustine at a concentration of about 15 mg/mL in n-propanol and mannitol at a concentration of about 25.5 mg/mL in water. Included in this embodiment are the spray dried preparations made from such bendamustine formulations.

Also provided are pre-drying pharmaceutical compositions of bendamustine. A preferred set of pre-dried compositions includes bendamustine HCl about 15 mg/mL in n-propanol, mannitol about 25.5 mg/mL in water. In certain embodiments, provided is a formulation for continuous drying comprising bendamustine at a concentration of about 0.25 to about 300 mg/mL, polyvinylpyrolidone at a concentration of about 0.25 mg/mL to about 500 mg/mL and a non-aqueous solvent. In certain embodiments, provided is a formulation for continuous drying comprising bendamustine at a concentration of about 0.25 to about 200 mg/mL, polyvinylpyrolidone at a concentration of about 0.25 mg/mL to about 500 mg/mL and a non-aqueous solvent. In certain embodiments, provided is a formulation for continuous drying comprising bendamustine at a concentration of about 0.25 to about 300 mg/mL, hydroxypropyl methylceullulose acetate succinate (HPMC-AS) at a concentration of about 0.25 mg/mL to about 500 mg/mL and a non-aqueous solvent. In certain embodiments, provided is a formulation for continuous drying comprising bendamustine at a concentration of about 0.25 to about 200 mg/mL, hydroxypropyl methylceullulose acetate succinate (HPMC-AS) at a concentration of about 0.25 mg/mL to about 500 mg/mL and a non-aqueous solvent.

Methods of Treatment

In another aspect, provided herein are methods of treating a medical condition in a patient. The methods comprise administering a therapeutically effective amount of a pharmaceutical composition provided herein where the condition is amenable to treatment with the pharmaceutical composition. Some conditions amenable to treatment with the compositions include chronic lymphocytic leukemia (CLL), Hodgkin's disease, non-Hodgkin's lymphoma (NHL), multiple myeloma (MM), breast cancer, small cell lung cancer, hyperproliferative disorders, and autoimmune diseases. Preferred conditions include NHL, CLL, breast cancer, and MM. Preferred autoimmune diseases include rheumatoid arthritis, multiple sclerosis and lupus.

Also provided are methods of using the pharmaceutical compositions or pharmaceutical preparations in the manufacture of a therapeutic agent for the treatment of a medical condition, as described herein, in a patient that comprise administering a therapeutically effective amount of a pharmaceutical composition where the condition is amenable to treatment with the pharmaceutical composition.

Also provided are methods of treatment in which the pharmaceutical compositions are in combination with one or more anti-neoplastic agents where the antineoplastic agent is administered prior, concurrently, or subsequent to the administration of the pharmaceutical composition. Preferred antineoplastic agents include antibodies specific for CD20, for example, rituximab, ibritumomab, tiuxetan, ofatumumab and tositumomab.

The compositions provided herein can be marketed in pharmaceutical dosage form. The pharmaceutical dosage form, typically in the form of a vial, can be any suitable container, such as ampoules, syringes, co-vials, which are capable of maintaining a sterile environment. Such containers can be glass or plastic, provided that the material does not interact with the bendamustine composition. The closure is typically a stopper, most typically a sterile rubber stopper, preferably a bromobutyl rubber stopper, which affords a hermetic seal.

The compositions can be reconstituted with water, preferably Sterile Water for Injection, or other sterile fluid such as co-solvents, to provide an appropriate solution of bendamustine for administration, as through parenteral injection following further dilution into an appropriate intravenous admixture container, for example, normal saline.

In the methods of treatment, the reconstituted active bendamustine can be administered to a patient in need thereof by intravenous administration according to standard techniques.

Kits

Also provided are kits for use in methods of treatment of proliferative or autoimmune disorders. The kits can include a composition provided herein, a second agent or composition, and instructions providing information to a health care provider regarding usage for treating the disorder. Instructions can be provided in printed form or in the form of an electronic medium such as a floppy disc, CD, or DVD, in the form of a website address where such instructions can be obtained, or in the form of a website where a smart phone, tablet, or wearable electronic device application can be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., spray dried) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging can have sufficiently low density to permit sterilization of the contents.

Second Therapeutic Agents

In certain embodiments, the compositions provided herein are useful in methods of treatment of a proliferative or autoimmune disorder, that comprises further administration of a second agent effective for the treatment of the disorder in a subject in need thereof. The second agent can be any agent known to those of skill in the art to be effective for the treatment of the disorder, including those currently approved by the U.S. Food and Drug Administration or other regulatory agencies worldwide.

In certain embodiments, a compound provided herein is administered in combination with one second agent. In further embodiments, a second agent is administered in combination with two second agents. In still further embodiments, a second agent is administered in combination with two or more second agents.

Anti-neoplastic agents which can be utilized in the methods described herein and in combination with the formulations described herein include those provided in the Merck Index 11, pp 16-17, Merck & Co., Inc. (1989) and The Chemotherapy Source Book (1997). Both books are widely recognized and readily available to the skilled artisan.

There are large numbers of antineoplastic agents available in commercial use, in clinical evaluation and in pre-clinical development, which can be selected for treatment of neoplasia by combination drug chemotherapy. Such antineoplastic agents fall into several major categories, namely, antibiotic-type agents, covalent DNA-binding drugs, antimetabolite agents, hormonal agents, including glucocorticoids such as prednisone and dexamethasone, immunological agents, interferon-type agents, differentiating agents such as the retinoids, pro-apoptotic agents, and a category of miscellaneous agents, including compounds such as antisense, small interfering RNA, and the like. Alternatively, other anti-neoplastic agents, such as metallomatrix proteases (MMP) inhibitors, SOD mimics or $\alpha_v\beta_3$ inhibitors can be used.

One family of antineoplastic agents which can be used in methods described herein and in combination with the formulations described herein consists of antimetabolite-type antineoplastic agents. Suitable antimetabolite antineoplastic agents can be selected from the group consisting of alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which can be used in methods described herein and in combination with the formulations described herein consists of covalent DNA-binding agents. Suitable alkylating-type antineoplastic agents can be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, cannustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol.

Another family of antineoplastic agents which can be used in methods described herein and in combination with the formulations described herein disclosed herein consists of antibiotic-type antineoplastic agents. Suitable antibiotic-type antineoplastic agents can be selected from the group consisting of Taiho 4181-A, aclarubicin, actinomycin D, actinoplanone, alanosine, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-Al, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which can be used in methods described herein and in combination with the formulations described herein include a miscellaneous family of antineoplastic agents selected from the group consisting of alpha-carotene, alpha-difluoromethyl-arginine, acitretin, arsenic trioxide, Avastin® (bevacizumab), Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-ll, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, epothionesTsumura EPMTC, erbitux, ergotamine, erlotnib, etoposide, etretinate, fenretinide, Fujisawa FR-57704, gallium nitrate, genkwadaphnin, Gleevec® (imatnib), Chugai GLA-43, Glaxo GR-63178, gefitinib, grifolan NMF-5N, hexadecylphosphocholine, Green Cross HO-221, homoharringtonine, hydroxyurea, BTG ICRF-187, ibrutinib, idelalisib (Zydelig), indanocine, ilmofosine, isoglutamine, isotretinoin, Jak-kinase inhibitors, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, mefloquine, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, Rituxan® (and other anti CD20 antibodies, e.g. Bexxar®, Zevalin®), SmithKline SK&F-104864, statins (Lipitor® etc.), Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Thalidomide, Thalidomide analogs, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534, Zometa®.

Examples of radioprotective agents which can be used in combination chemotherapy are AD-5, adchnon, amifostine analogues, detox, dimesna, 1-102, MM-159, N-acylated-dehydroalanines, TGF-Genentech, tiprotimod, arnifostine, WR-151327, FUT-187, ketoprofen transdermal, nabumetone, superoxide dismutase (Chiron and Enzon).

Methods for preparation of the antineoplastic agents described above can be found in the literature. Methods for preparation of doxorubicin, for example, are described in U.S. Pat. Nos. 3,590,028 and 4,012,448. Methods for preparing metallomatrix protease inhibitors are described in European Pat. No. EP 780386. Methods for preparing $\alpha_v\beta_3$ inhibitors are described in PCT International Patent Application Pub. No. WO 97/08174.

Preferred anti-neoplastic agents include, without limitation, one or more of daunorubicin, bleomycin, vincristine, doxorubicin, dacarbazine, prednisolone, mitoxantrone, prednisone, methotrexate, 5-flurouracil, dexamethasone, thalidomide, thalidomide derivatives, 2ME2, Neovastat, R 11 5777, arsenic trioxide, bortezomib, tamoxifen, G3139 (antisense), SU5416, mitomycin, anti-CD20 antibodies, such as Rituxan® and R-etodolac.

Preferred drug regimens for which the present formulation can be used in conjunction with or as a replacement for one or more of the components includes, without limitation, ABVD (doxorubicin, bleomycin, vincristine, dacarbazine), DBV (daunorubicin, belomycin, vincristine), CVPP (cyclophosphamide, vinblastine, procarbazine, prednisolone), COP (cyclophosphamide, vincristine, prednisolone), CHOP (cyclophosphamide, doxorubicin, vincristine and prednisone) and CMF (cyclophosphamide, methotrexate, 5-fluorouracil). Additional regimens are given in Table A below.

TABLE A

| Cancer Therapeutic Regimens | | |
|---|---|---|
| Abbreviation | Drugs Used | Disease |
| AC | Doxorubicin, Cyclophosphamide | Breast cancer |
| CFM (CF, FNC) | Cyclophosphamide, Fluorouracil, Mitaxantrone | Breast cancer |
| CMF | Cyclophosphamide Methotrexate, Fluorouracil | Breast cancer |
| NFL | Mitoxantrone, Fluorouracil, Leucovorin | Breast cancer |
| Sequential Dox-CMF | Doxorubicin | Breast cancer |
| VATH | Vinblastine, Doxorubicin, Thiotepa, Fluoxymesterone | Breast Cancer |
| EMA-86 | Etoposide, Mitoxantrone, Cytarabine | AML (induction) |
| 7 + 3 | Cytarabine WITH Daunorubicin OR Idarobicin OR Mitoxantrone | AML (induction) |
| 5 + 2 | Cytarabine WITH Daunorubicin OR Mitoxantrone | AML (induction) |
| HiDAC | Cytarabine | AML (post-remission) |
| ABVD | Doxorubicin, Bleomycin, Vinblastine, Dacarbazine | Hodgkin's |
| ChlVPP | Chlorambucil, Vinblastine, Procarbazine, Prednisone | Hodgkin's |
| EVA | Etoposide, Vinblastine, Doxorubicin | Hodgkin's |
| MOPP | Mechlorethamine, Vincristine, Procarbazine, Prednisone | Hodgkin's |
| MOPP/ABV Hybrid | Mechlorethamine, Vincristine, Procarbazine, Prednisone, Doxorabicin, Bleomycin, Vinblastine | Hodgkin's |
| MOPP/ABVD | Mechlorethamine, Doxorubicin, Vinblastine, Bleomycin, Etoposide, Prednisone | Hodgkin's |
| CNOP | Cyclophosphamide, Mitoxantrone, Vincristine, Prednisone | Non-Hodgkin's |
| COMLA | Cyclophosphamide, Vincristine, Methotrexate, Leucovorin, Cytarabine | Non-Hodgkin's |
| DHAP | Dexamethasone, Cisplatin, Cytarabine | Non-Hodgkin's |
| ESHAP | Etoposide, Methylprednisilone, Cisplatin, Cytarabine | Non-Hodgkin's |
| MACOP-B | Methotrexate, Leucovorin, Doxorubicin, Cyclophosphamide, Vincristine, Prednisone, Bleomycin, Septra, Ketoconazole | Non-Hodgkin's |
| m-BACOD | Methotrexate, Leucovorin, Bleomycin, Doxorubicin, Cyclophosphamide, Vincristine, Dexamethasone | Non-Hodgkin's |

TABLE A-continued

| Cancer Therapeutic Regimens | | |
|---|---|---|
| Abbreviation | Drugs Used | Disease |
| MINE-ESHAP | Mesna, Ifosfamide, Mitoxantrone, Etoposide | Non-Hodgkin's |
| NOVP | Mitoxantrone, Vinblastine, Prednisone, Vincristine | Non-Hodgkin's |
| ProMACE/cytaBOM | Prednisone, Doxorubicin, Cyclophosphamide, Etoposide, Cytarabine, Bleomycin, Vincristine, Methotrexate, Leucovorin, Septra | Non-Hodgkin's |
| M2 | Vincristine, Carmustine, Cyclophosphamide, Melphalan, Prednisone | Multiple Myeloma |
| MP | Melphalan, Prednisone | Multiple Myeloma |
| VAD | Vincristine, Doxorubicin, Dexamethasone | Multiple Myeloma |
| VBMCP | Vincristine, Carmustine, Melphalan, Cyclophosphamide, Prednisone | Multiple Myeloma |

The embodiments provided herein are illustrated by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of the American Institute of Chemical Engineers or the Journal of Biological Chemistry.

Specifically, but without limitation, the following abbreviations can be used in the examples and throughout the specification: g or gr (grams); mg or mgr (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All steps are conducted at room temperature unless otherwise noted. Specific methodologies illustrated herein are intended to exemplify the applicable compositions and processes through the use of specific examples and do not limit the scope of the disclosure.

Materials: Bendamustine HCL, (Tianjin Pharmacn Medical Technology Co, Ltd, Batch #130801); Mannitol, Pearlitol 160C (Roquette, Lot #52305973); PVP, Plasdone K-17 (Ashland, Product Code 1172625, Lot #052305973); HPMCAS, Aquasolve HPMC-AS MF (Ashland, Product Code834121, Lot #ASHMA 1004F); Ethyl Alcohol, USP grade UN1170, (200 proof) (Koptec, PN V1001); n-propanol (Macron Fine Chemicals, Batch #0000040691); Methanol, (Omnisolv, MX0488-6).

Equipment: Agilent 1100 series equipped with a UV detector; Zorbax SB-C18, 4.6×250 mm, 5 um; Rigaku Smart-Lab X-ray diffraction system, TA Instruments Q2000 DSC system, TA Instruments Q50 TG system, Leica M80 stereo microscope with a PAXcam3 digital camera, Buchi B-191 spray drier, PANalytical X'Pert PRO MPD difractometer using an incident beam of Cu Kα radiation produced using a long, fine-focus source and a nickel filter.

Example 1: Spray-Drying Development

Several pre-drying aqueous and non-aqueous formulations were prepared at various concentrations of bendamustine, organic solvent, mannitol, and water. The spray-drying run development was changed and optimized at each step for moisture content at the drier outlet, outlet temperature, particle flow characteristics and dry-powder reconstitution characteristics.

Based upon all of the information detailed above on solubility, stability, and ease of spray-drying, useful formulations include the following:

| | Concentrations | |
|---|---|---|
| Ingredient | Non-Aqueous Solution | Aqueous Solution |
| | Example 1-1 | |
| Bendamustine | 5-120 mg/ml | |
| NMP | q.s to desired volume | |
| Mannitol | | 5-220 mg/ml |
| Water | | q.s. to desired volume |
| | Example 1-2 | |
| Bendamustine | 5-300 mg/ml | |
| DMSO | q.s to desired volume | |
| Mannitol | | 5-220 mg/ml |
| Water | | q.s. to desired volume |
| | Example 1-3 | |
| Bendamustine | 5-100 mg/ml | |
| Dimethylformamide | q.s to desired volume | |
| Mannitol | | 5-220 mg/ml |
| Water | | q.s. to desired volume |
| | Example 1-4 | |
| Bendamustine | 5-80 mg/ml | |
| N-propanol | q.s to desired volume | |
| Mannitol | | 5-220 mg/ml |
| Water | | q.s. to desired volume |
| | Example 1-5 | |
| Bendamustine | 5-80 mg/ml | |
| Methanol | q.s to desired volume | |
| Mannitol | | 5-220 mg/ml |
| Water | | q.s. to desired volume |
| | Example 1-6 | |
| Bendamustine | 5-80 mg/ml | |
| Ethanol | q.s to desired volume | |
| Mannitol | | 5-220 mg/ml |
| Water | | q.s. to desired volume |

-continued

| Ingredient | Concentrations Non-Aqueous Solution | Aqueous Solution |
|---|---|---|
| Example 1-7 | | |
| Bendamustine | 5-150 mg/ml | |
| Tert-Butyl Alcohol | q.s to desired volume | |
| Mannitol | | 5-220 mg/ml |
| Water | | q.s. to desired volume |

Example 2: HPLC Procedures

Bendamustine and bendamustine degradation products were measured by high performance liquid chromatography according to Method 1 or Method 2, below.

Method 1

| Parameter | Value |
|---|---|
| Column | Zorbax SB-C18, 4.6 × 250 mm, 5 um with C18 4 × 3 mm Phenomenex Security Guard |
| Column Temperature | 30° C. |
| Detector wavelength | 230 nm |
| Mobile Phase A: | 0.1% TFA in water |
| Mobile Phase B: | 0.1% TFA in water:ACN (1:1) |
| Gradient: | 0 min, 20% B |
| | 1 min, 20% B |
| | 24 min, 90% B |
| | 30 min, 90% B |
| | 31 min, 20% B |
| Injection Volume: | 10 uL |
| Flow rate: | 1.0 mL/min |
| Run time: | 36 min |

Method 2

| Parameter | Value |
|---|---|
| Column | Kinetex 2.6 u C18, 100 A, 4.6 × 100 mm (Phenomenex) |
| Column Temperature | 30° C. |
| Detector wavelength | 230 nm |
| Mobile Phase A: | 0.1% TFA in water |
| Mobile Phase B: | 0.1% TFA in water:ACN (1:1) |
| Gradient: | 0 min, 20% B |
| | 1 min, 20% B |
| | 27 min, 90% B |
| | 35 min, 90% B |
| | 36 min, 20% B |
| | 43 min, 20% B |
| Injection Volume: | 10 uL |
| Flow rate: | 0.6 mL/min |
| Run time: | 43 min |

Results

The retention times for some Bendamustine impurities using Method 1 described above, are shown in Table 1.

TABLE 1

Retention Time for Bendamustine and impurities using HPLC Method 1

| Sample Name | Retention Time (min) |
|---|---|
| HP2 | 6.8 |
| HP1 | 12.8 |
| Bendamustine | 20.3 |
| Bendamustine methlylester | 21.7 |
| Bendamustine dimer | 23.3 |

The retention times for Bendamustine impurities using Method 2 described above are shown in Table 2.

TABLE 2

Retention Time for Bendamustine and impurities using HPLC Method 2

| Sample Name | Retention Time (min) |
|---|---|
| HP1 | 11.2 |
| Bendamustine | 20.4 |
| Dimer | 24.3 |

Example 3: Single Container Mannitol Batches

In order to develop a baseline, two pharmaceutical compositions were obtained by dissolving Bendamustine Hydrochloride API in a 10% (v/v) ethanol/water solution. Batch 1 was obtained by dissolving 600 mg of Bendamustine HCL and 1020 mg of Mannitol in 60 ml of 10% (v/v) ethanol water solution. Thus, the Total Solids ratio for this batch was 2.8%. Batch 2 was obtained by dissolving 400 mg of Bendamustine HCL and 680 mg of Mannitol in 80 ml of 10% (v/v) ethanol water solution. Thus the Total Solids ratio for this batch was 1.4% (w/w). For both batches the ratio of mannitol to bendamustine is around 1.7.

The system used to further process both batches is shown in FIG. 1. In both cases only one container feed line was used, namely the non-aqueous Bendamustine feed line. In both cases, however, a 10% (v/v) ethanol water solution instead of a non-aqueous pure organic solution was pumped through the feed line.

Batch 1 was fed into the downstream spray dry system after mixing for approximately 10 minutes to establish complete dissolution of the solids. During feeding, the solution was being stirred via a magnetic stirrer and its temperature was around 20° C. Batch 2 was aged for 24 hrs before being fed into the downstream spray drying system in a similar was as batch 1.

As is well known to persons skilled in the art, spray drying optimization involves a multitude of process parameters. The values for these parameters mentioned in these examples are in no way to be considered to limit the scope of the embodiments provided herein in any manner. The values for some of these parameters are shown in Table 3A.

TABLE 3A

| Process Parameters for Example 3 | | | | | | | |
|---|---|---|---|---|---|---|---|
| | Feed rate (g/min) | Atomizer Pressure (psi) | Atomizer gas flow (g/sec) | ALR ratio | Temp Inlet (° C.) | Temp outlet (° C.) | Run Time (min) |
| Batch 1 | 1.48 | 51 | 0.57 | 23.1 | 115 | 86 | 42 |
| Batch 2 | 2.43 | 40 | 0.48 | 11.9 | 102 | 73 | 32 |

The spray dried powder collected for both batches had white color. It was flowing nicely and constituted of small particles. The batches were tested for residual moisture, residual solvent (via TGA) and concentration of degradants. (HP2 related compounds, HP1 related compounds, dimer, methylester and ethylester of Bendamustine.). The results can be seen in Table 3B.

TABLE 3B

| Test Results for Example 3 | | | | | | |
|---|---|---|---|---|---|---|
| | HP2 (% Area) | HP1 (% Area) | Bendamustine (% Area) | Dimer (% Area) | Moisture (% w/w) | Residual Solvent (% w/w) |
| Batch 1 | ND | 0.45 | 99.26 | ND | 0.38 | 0.55 |
| Batch 2 | 0.94 | 22.5 | 74.7 | ND | 0.45 | 0.50 |

From the results, it was found that even with a hold time of the pre-drying solution of less than 1 hour, there was still a noticeable amount of the HP1 degradant in the final powder. It was also remarkably found that the powder flow characteristics of Batch 2 were noticeable different compared to other mannitol formulated batches. This was attributed to the elevated concentrations of primarily HP1 and HP2 and possibly other degradants contained in the spray dried powder. This shows that the existence of degradants does have a material effect on the morphological and physical characteristics of the ensuing powder. Furthermore, lack of ensuing batch uniformity indicates that spray drying may not be a feasible alternative when running under conditions between Batch 1 and Batch 2.

Example 4: Single Container Runs with Other Excipients. (PVP and HPMC-AS)

One of the reasons for using water in the previous formulations was to ensure a sufficient dissolution of mannitol (which is not dissolved in alcohols). There are other excipients however, that do dissolve in alcohols. Two examples of such excipients are polyvinylpyrrolidone (PVP) and HPMC-AS. In this case bendamustine and the excipient (PVP or HPMC-AS) were dissolved in ethanol and spray dried the same way as in Example 3

Batch 3 was obtained by dissolving 600 mg of bendamustine HCL and 3000 mg of Plasdone K-17 (polyvinylpyrrolidone, PVP) in 120 ml of pure ethanol. The ratio of PVP to bendamustine is 5:1. Thus, the Total Solids ratio for this batch was 3.0%. Batch 4 was obtained by dissolving 300 mg of bendamustine HCL and 900 mg of HPMC-AS in 40 ml of pure methanol. The ratio of HPMC-AS to bendamustine was 3:1. The Total Solids ratio for batch 4 was 3.8%.

TABLE 4

Process Parameters for Example 5

| | Feed rate (g/min) | Atomizer Pressure (psi) | Atomizer gas flow (g/sec) | ALR ratio | Temp Inlet (° C.) | Temp outlet (° C.) | Run Time (min) |
|---|---|---|---|---|---|---|---|
| Batch 3 | 2.09 | 50 | 0.57 | 16.3 | 81 | 63 | 45.7 |
| Batch 4 | 2.05 | 40 | 0.49 | 14.3 | 80 | 63 | 15.25 |

The spray dried powder obtained was consisting of fine particles of white color. It was noted that the particles exhibited clear signs of static electricity. The batches were tested for residual moisture, residual solvent (via TGA) and concentration of degradants. (HP2 related compounds, HP1 related compounds, Dimer, Methylester and EthylEster of Bendamustine.). The results can be seen in Table 5.

Figure 5:
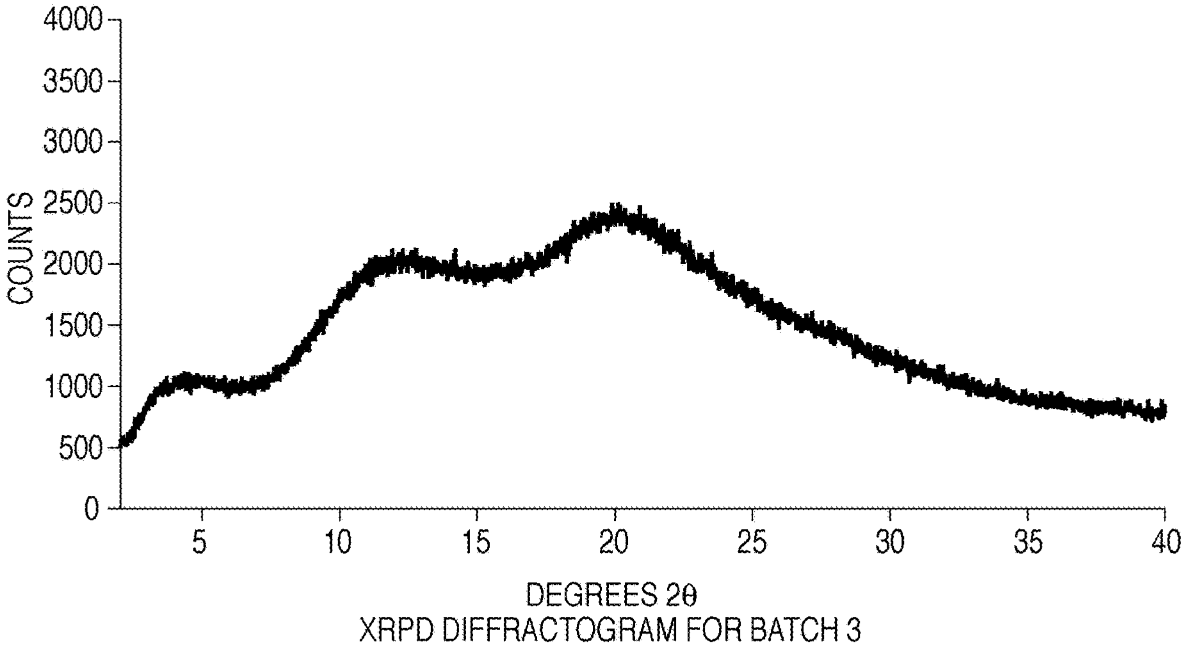
FIG. 5 provides an XRPD diffractogram for a spray dried powder produced from 600 mg of Bendamustine HCL and 3000 mg of Plasdone K-17 (Polyvinylpyrolidone, PVP) in 120 ml of pure ethanol.
Figure 6:
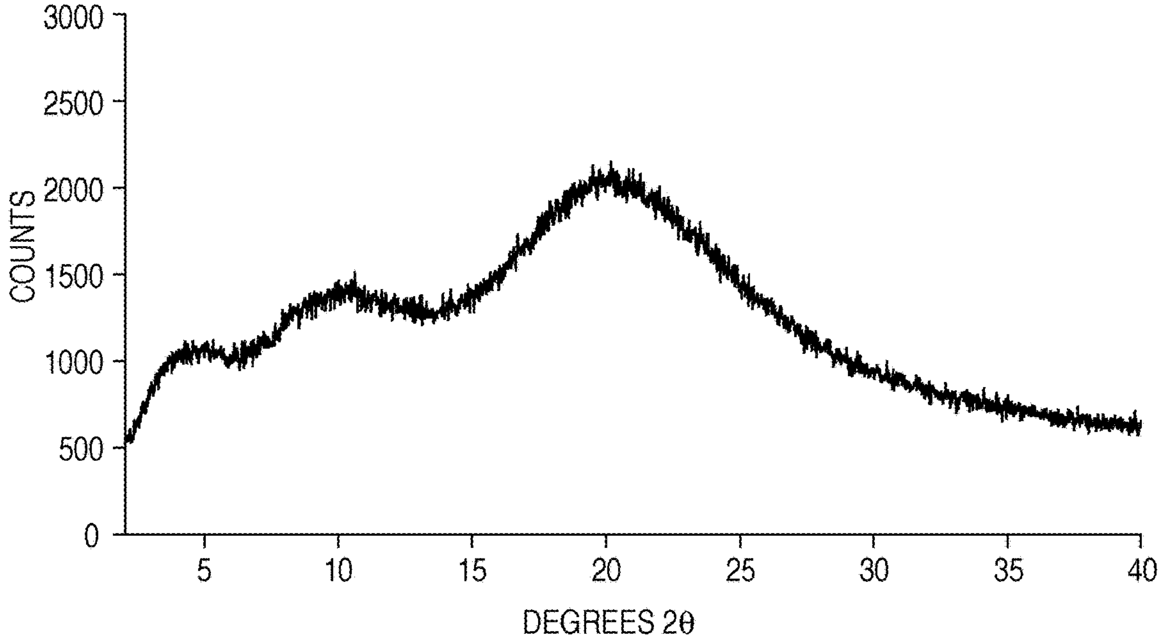
FIG. 6 provides an XRPD diffractogram for a spray dried powder produced from 300 mg of Bendamustine HCL and 900 mg of HPMC-AS in 40 ml of pure methanol.

Solid phase characterization tests were conducted on Batch 3 and 4. XRPD diffractograms can be seen in FIGS. 5 and 6 for Batch 3 and 4 respectively. From these diffractograms it was found that although Bendamustine HCL has a tendency to crystallize, both solid dispersions with PVP and HPMC-AS were amorphous.

TABLE 5

Test Results for Example 5

| | HP2 (% Area) | HP1 (% Area) | Bendamustine (% Area) | Dimer (% Area) | Moisture (% w/w) | Residual Solvent (% w/w) |
|---|---|---|---|---|---|---|
| Batch 3 | ND | ND | 100.0 | ND | NA (*) | 0.54 (*) |
| Batch 4 | ND | ND | 100.0 | ND | 1.105 | 0.655% |

Notes:
(*) Moisture not measured. 0.54 is for both moisture and residual solvent.

Testing multiple samples with XRPD resulted in essentially identical diffractograms indicating dry powder batch uniformity.

Figure 7:
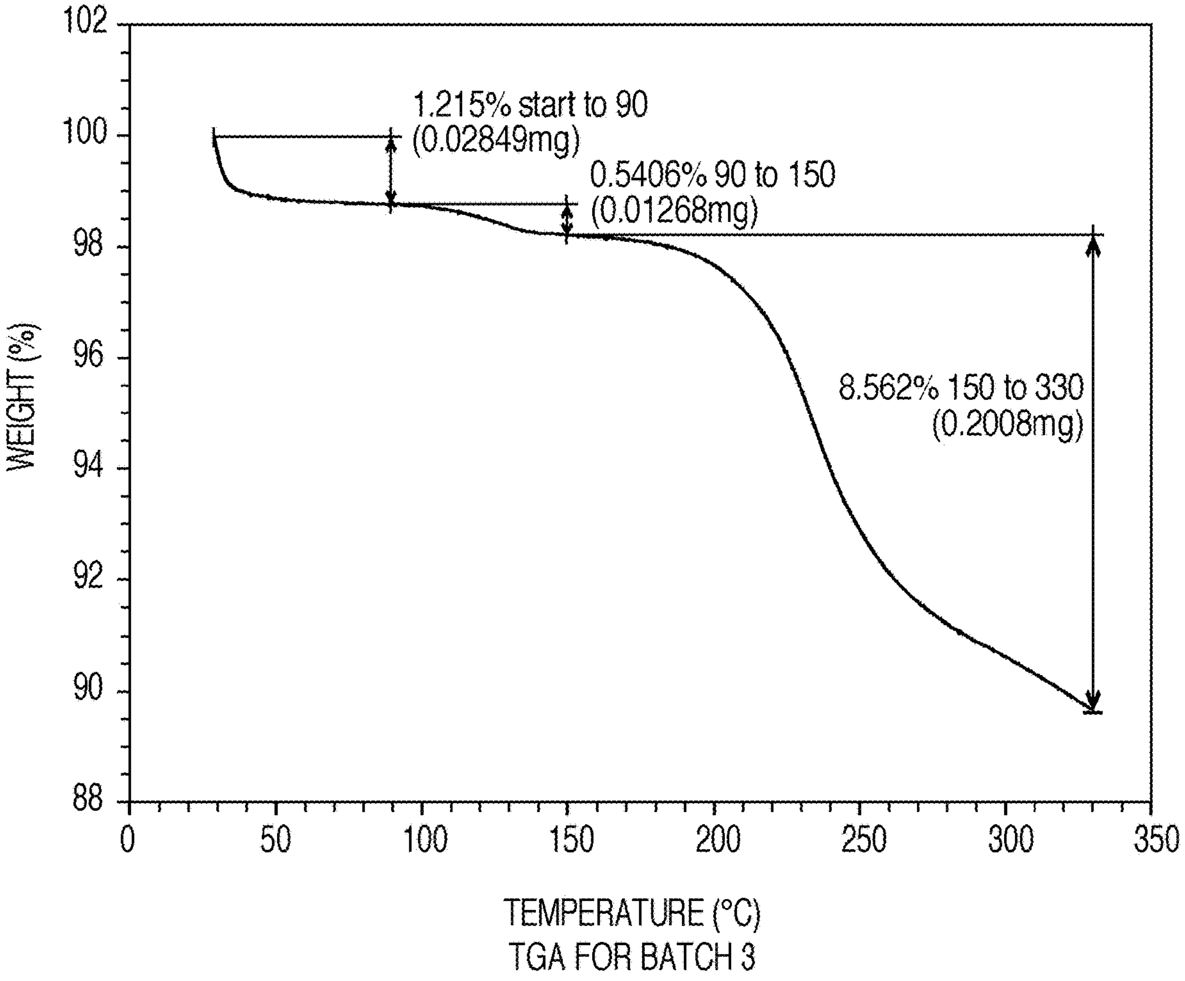
FIG. 7 provides Thermogravimetric Analysis (TGA) of a spray dried powder produced from 600 mg of Bendamustine HCL and 3000 mg of Plasdone K-17 (Polyvinylpyrolidone, PVP) in 120 ml of pure ethanol.
Figure 8:
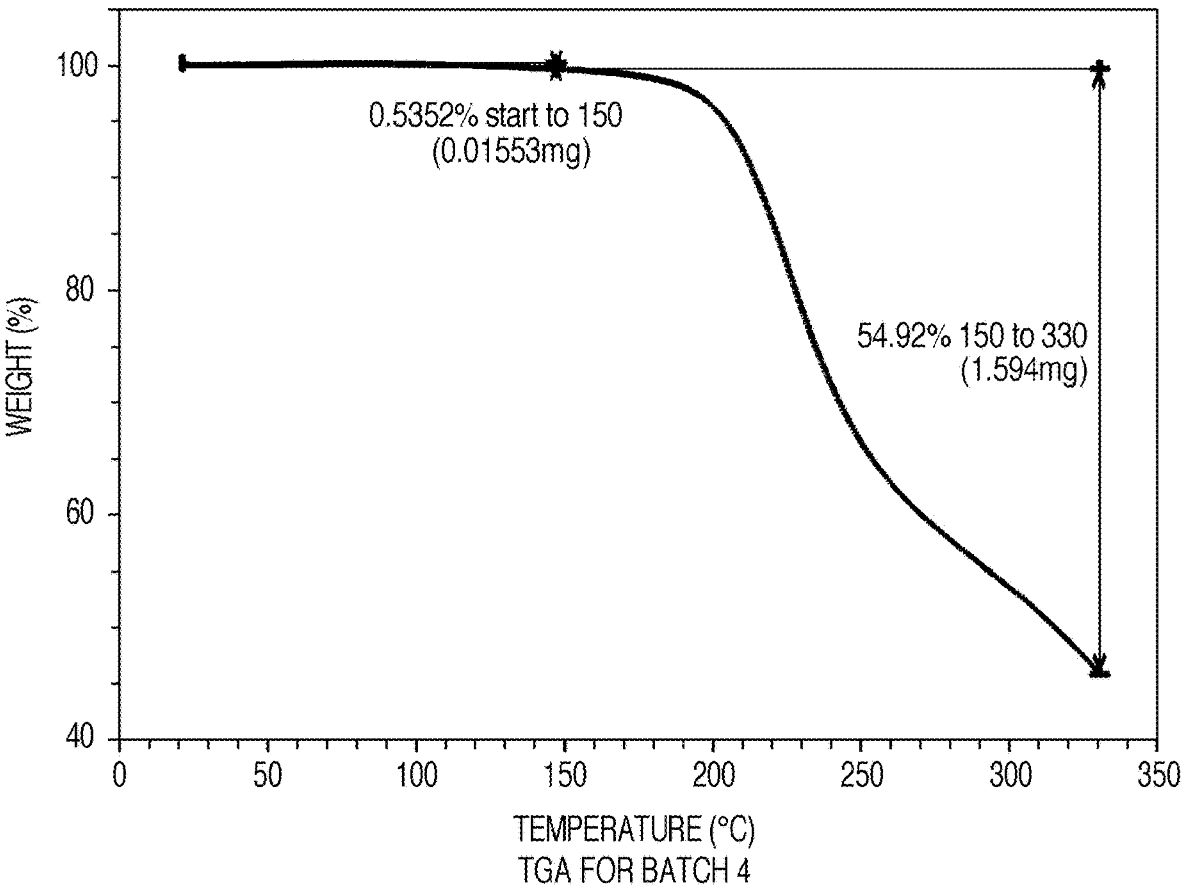
FIG. 8 provides Thermogravimetric Analysis (TGA) of a spray dried powder produced from 300 mg of Bendamustine HCL and 900 mg of HPMC-AS in 40 ml of pure methanol.

FIGS. 7 and 8 show the Thermogravimetric Analysis (TGA) for Batch 3 and 4 respectively. Karl Fisher testing showed that the moisture content of Batch 3 was 1.105% (w/w). TGA shows that both water and organic solvent content in the dry powder is 1.76% (w/w). The organic residual solvent in the dry powder is, therefore, 0.655%.

TABLE 6

HPLC results at t = 2 months

| | HP2 (% area) | HP1 (% area) | Bendamustine (% area) | Dimer (% area) |
|---|---|---|---|---|
| Batch 3 | ND | ND | 100.0 | ND |
| Batch 4 | ND | ND | 100.0 | ND |

Notes:

Stability Tests

Stability tests were conducted on Batch 3 and 4, to assess the impact of moisture on the dry powder. Table 6 shows the HPLC results (Method 2) for Batches 3 and 4 after 2 months of storage at ambient conditions. It was found that even after 2 months, both batches 3 and 4 didn't exhibit any HP1 degradation. This was particularly surprising for Batch 3 since we were able to measure elevated moisture levels at t=0 compared to the other batches. This has been attributed to the beneficial properties of PVP in the dispersion which, in essence, kept bendamustine away from water and inhibiting hydrolysis.

Example 5: Paired (or Multiple) Container Runs with Mannitol

Two compositions were formulated in separate containers. For Batch 5, the aqueous composition consisted of 1190 mg of mannitol dissolved in 70 ml of water. The non-aqueous composition was formulated by dissolving 700 mg of bendamustine hydrochloride in 70 ml of ethanol. The ethanol/bendamustine solution can be cooled to minimize the extent of possible side reactions. For Batch 6, the aqueous composition was formulated consisting of 2380 mg of mannitol dissolved in 70 ml of water. The non-aqueous composition was formulated by dissolving 1400 mg of bendamustine in 70 ml of n-propanol. The propanol/bendamustine solution can be cooled to minimize the extent of possible side reactions. Both feed pumps (see FIG. 1) were set to have equal volumetric flow rates. Due to the experimental setting, however, slight deviations were observed. The observed mannitol to API ratio resulting from this unintended deviation was 1.9 for Batch 5 and 1.8 for Batch 6. Table 7 shows the process parameters for Batch 5 and Batch 6.

The spray dried powder obtained was consisting of fine particles of white color. The batches were tested for residual moisture, residual solvent (via TGA) and concentration of degradants. (HP2 related compounds, HP1 related compounds, dimer, methylester and ethylester of bendamustine.). The results can be seen in Table 8.

TABLE 7

Process Parameters for Example 5.

| | Feed rate (combined) (g/min) | Atomizer Pressure (psi) | Atomizer gas flow (g/sec) | ALR ratio | Temp Inlet (° C.) | Temp outlet (° C.) | Run Time (min) |
|---|---|---|---|---|---|---|---|
| Batch 5 | 2.43 | 50 | 0.57 | 14.0 | 115 | 85 | 49 |
| Batch 6 | 2.27 | 50 | 0.57 | 15.0 | 115 | 85 | 55 |

TABLE 8

Test Results for Example 5

| | HP2 (% Area) | HP1 (% Area) | Bendamustine (% Area) | Dimer (% Area) | Moisture (% w/w) | Residual Solvent (% w/w) |
|---|---|---|---|---|---|---|
| Batch 5 | ND | ND | 100.0 | ND | 0.32 | 0.07 |
| Batch 6 | ND | ND | 100.0 | ND | 0.34 | ND |

Figure 9:
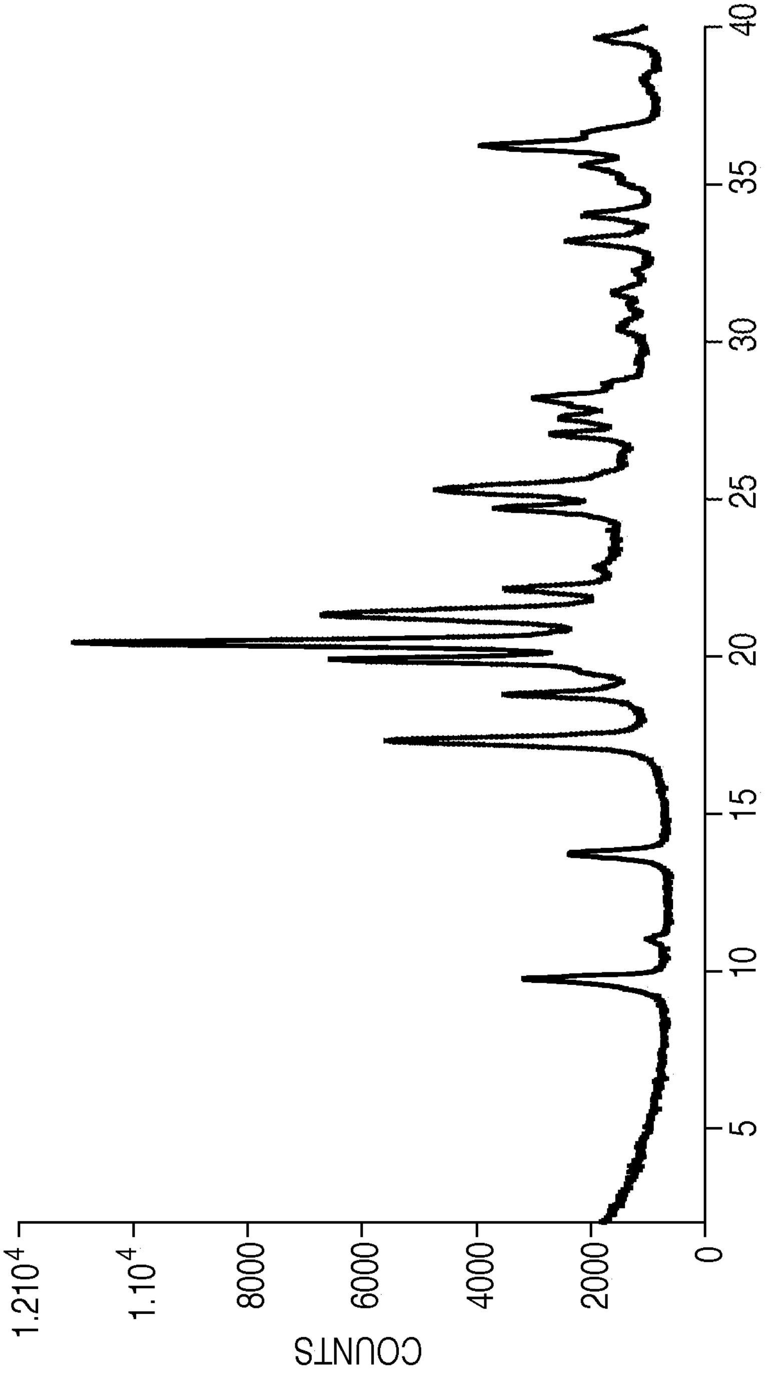
FIG. 9 provides an XRPD diffractogram of a spray dried powder produced from 1190 mg of mannitol dissolved in 70 ml of water and 700 mg of bendamustine hydrochloride in 70 ml of ethanol immediately following production.
Figure 10:
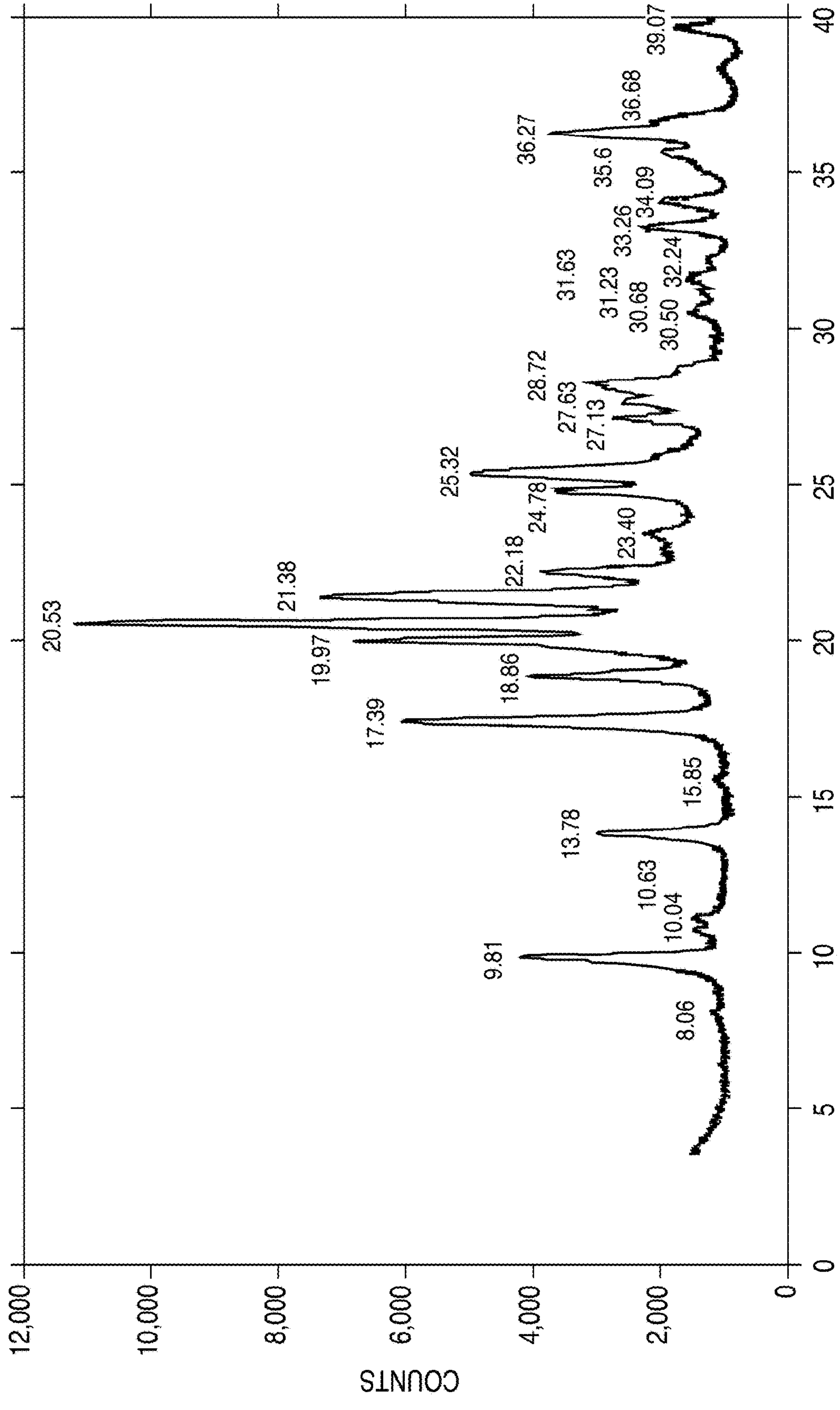
FIG. 10 provides an XRPD diffractogram of a spray dried powder produced from 1190 mg of mannitol dissolved in 70 ml of water and 700 mg of bendamustine hydrochloride in 70 ml of ethanol two months after production.

Solid phase characterization and stability tests were conducted on Batch 5. XRPD diffractograms for Batch 5 can be seen in FIG. 9 (right after production) and FIG. 10 (two months later). These diffractograms show that the solid dispersion remains stable after two months. It was also found that all crystalline peaks for the ensuing solid dispersion are related to mannitol (mannitol alpha and mannitol delta). None of the known peaks associated with crystalline bendamustine was observed. XRPD peak analysis for batch 5 resulted in the prominent peaks shown in Table 9.

Figure 11:
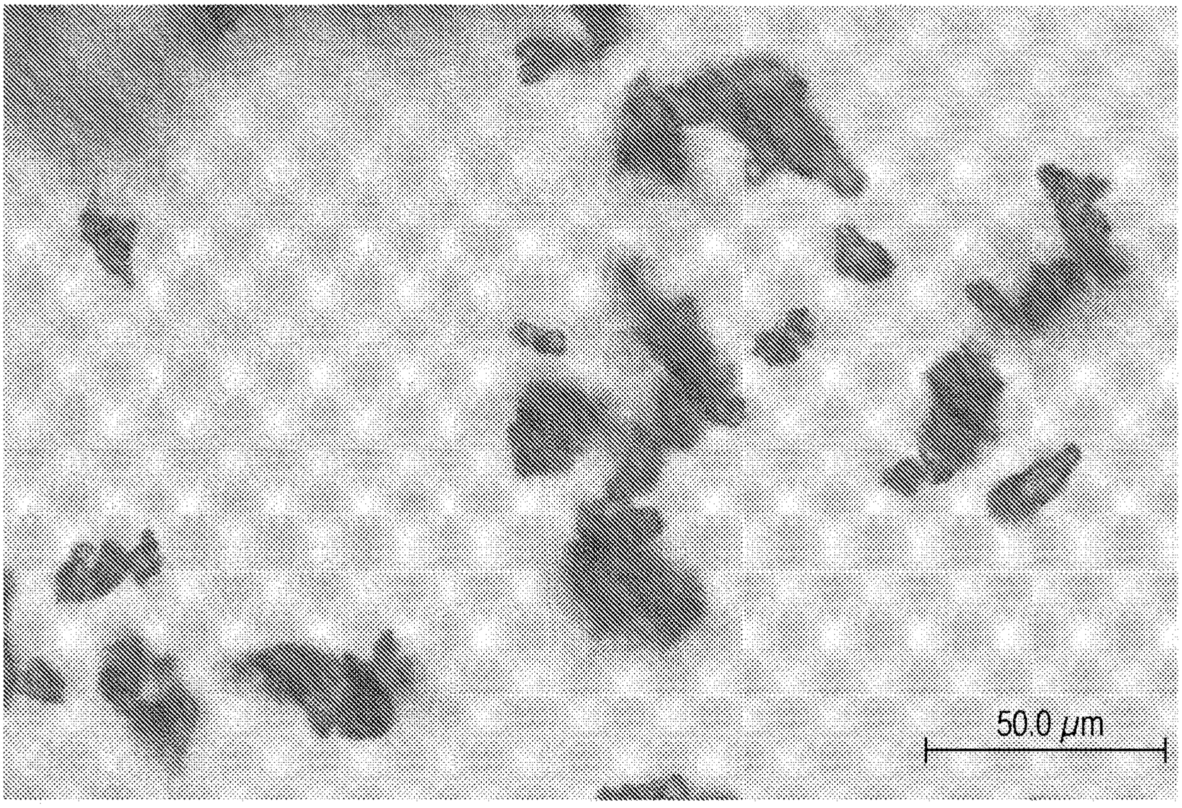
FIG. 11 provides an optical microscopy picture showing particles of a spray dried powder produced from 1190 mg of mannitol dissolved in 70 ml of water and 700 mg of bendamustine hydrochloride in 70 ml of ethanol.

An optical microscopy picture showing particles of Batch 5 can be seen in FIG. 11.

Figure 12:
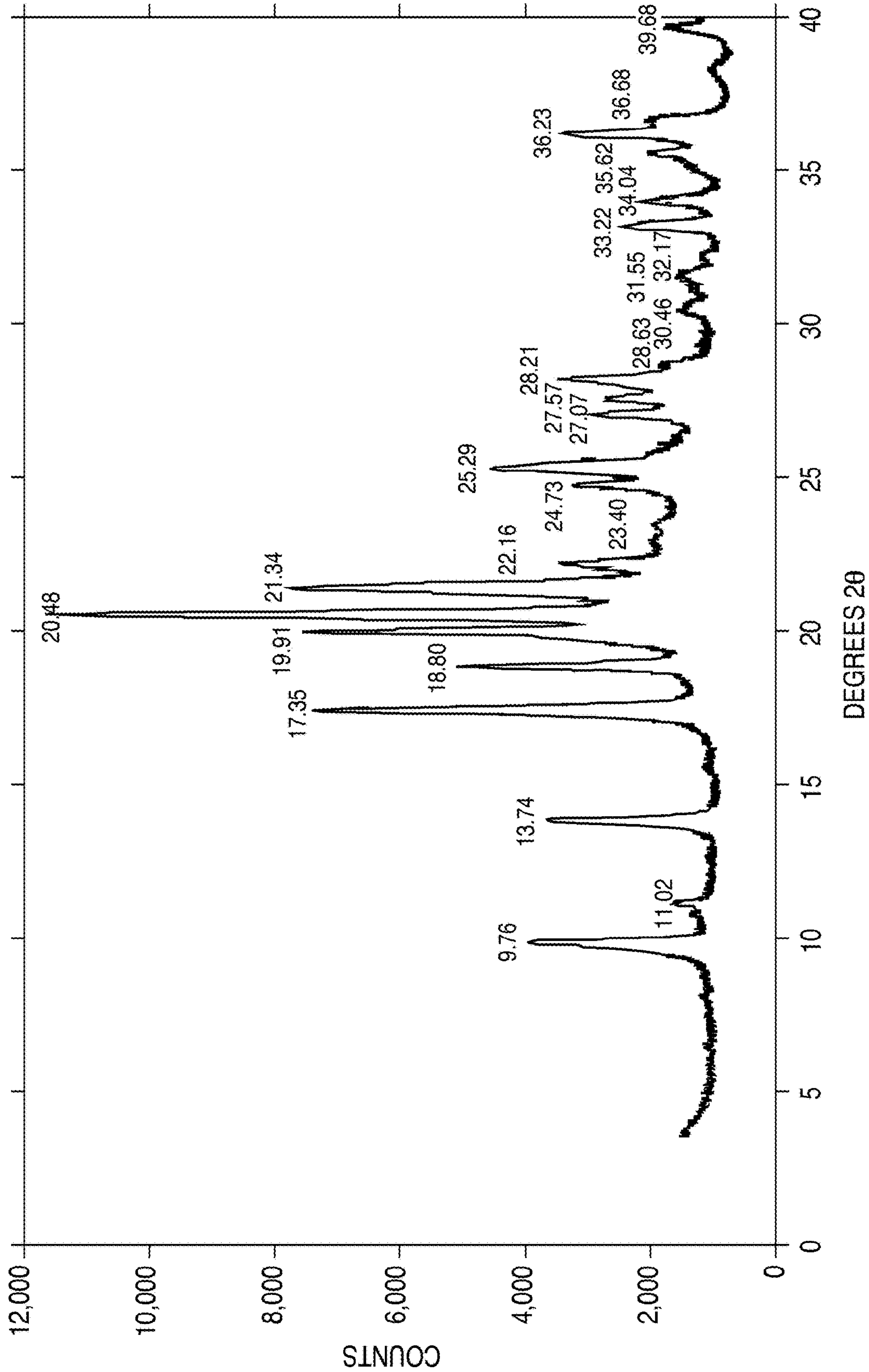
FIG. 12 provides an XRPD diffractogram of a spray dried powder produced from 2380 mg of mannitol dissolved in 70 ml of water and 1400 mg of bendamustine in 70 ml of n-propanol two months after production.

Solid phase characterization tests were conducted on Batch 6. XRPD diffractograms for Batch 6 can be seen in FIG. 12 (two months later). Again, it was found that no known crystalline peaks of bendamustine were observed. The solid dispersion again consisted of mannitol (mannitol alpha and mannitol delta). XRPD peak analysis for batch 6 resulted in the prominent peaks shown in Table 10. Note that a comparison between Table 9 and Table 10 points to the same peak locations with a slight intensity variation which can be explained by the differences in process parameters.

TABLE 9

| Prominent peaks for Batch 5 | | |
|---|---|---|
| 2θ | d space (Å) | Intensity (%) |
| 9.81 ± 0.2 | 9.013 ± 0.183 | 38 |
| 13.78 ± 0.2 | 6.422 ± 0.093 | 26 |
| 17.39 ± 0.2 | 5.094 ± 0.058 | 54 |
| 18.86 ± 0.2 | 4.701 ± 0.049 | 35 |
| 19.97 ± 0.2 | 4.442 ± 0.044 | 61 |
| 20.53 ± 0.2 | 4.323 ± 0.042 | 100 |
| 21.38 ± 0.2 | 4.153 ± 0.038 | 65 |
| 22.18 ± 0.2 | 4.005 ± 0.036 | 34 |
| 24.78 ± 0.2 | 3.590 ± 0.029 | 31 |
| 25.37 ± 0.2 | 3.507 ± 0.027 | 44 |
| 27.13 ± 0.2 | 3.284 ± 0.024 | 24 |
| 27.64 ± 0.2 | 3.225 ± 0.023 | 23 |
| 28.22 ± 0.2 | 3.160 ± 0.022 | 27 |
| 33.26 ± 0.2 | 2.692 ± 0.016 | 20 |
| 34.09 ± 0.2 | 2.628 ± 0.015 | 18 |
| 35.67 ± 0.2 | 2.515 ± 0.014 | 18 |
| 36.27 ± 0.2 | 2.475 ± 0.013 | 33 |
| 39.67 ± 0.2 | 2.270 ± 0.011 | 15 |

Figure 13:
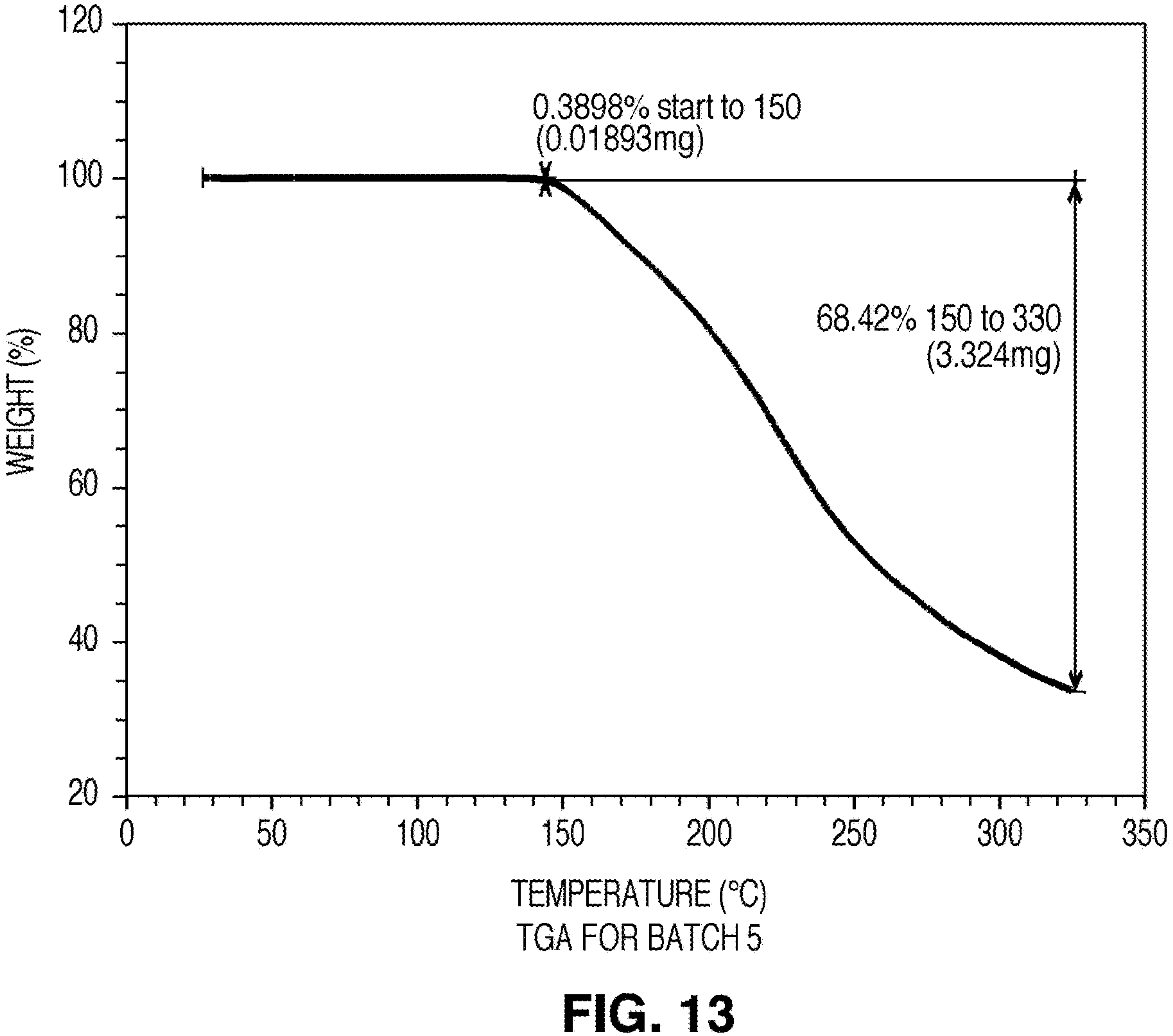
FIG. 13 provides Thermogravimetric Analysis (TGA) of a spray dried powder produced from 1190 mg of mannitol dissolved in 70 ml of water and 700 mg of bendamustine hydrochloride in 70 ml.
Figure 14:
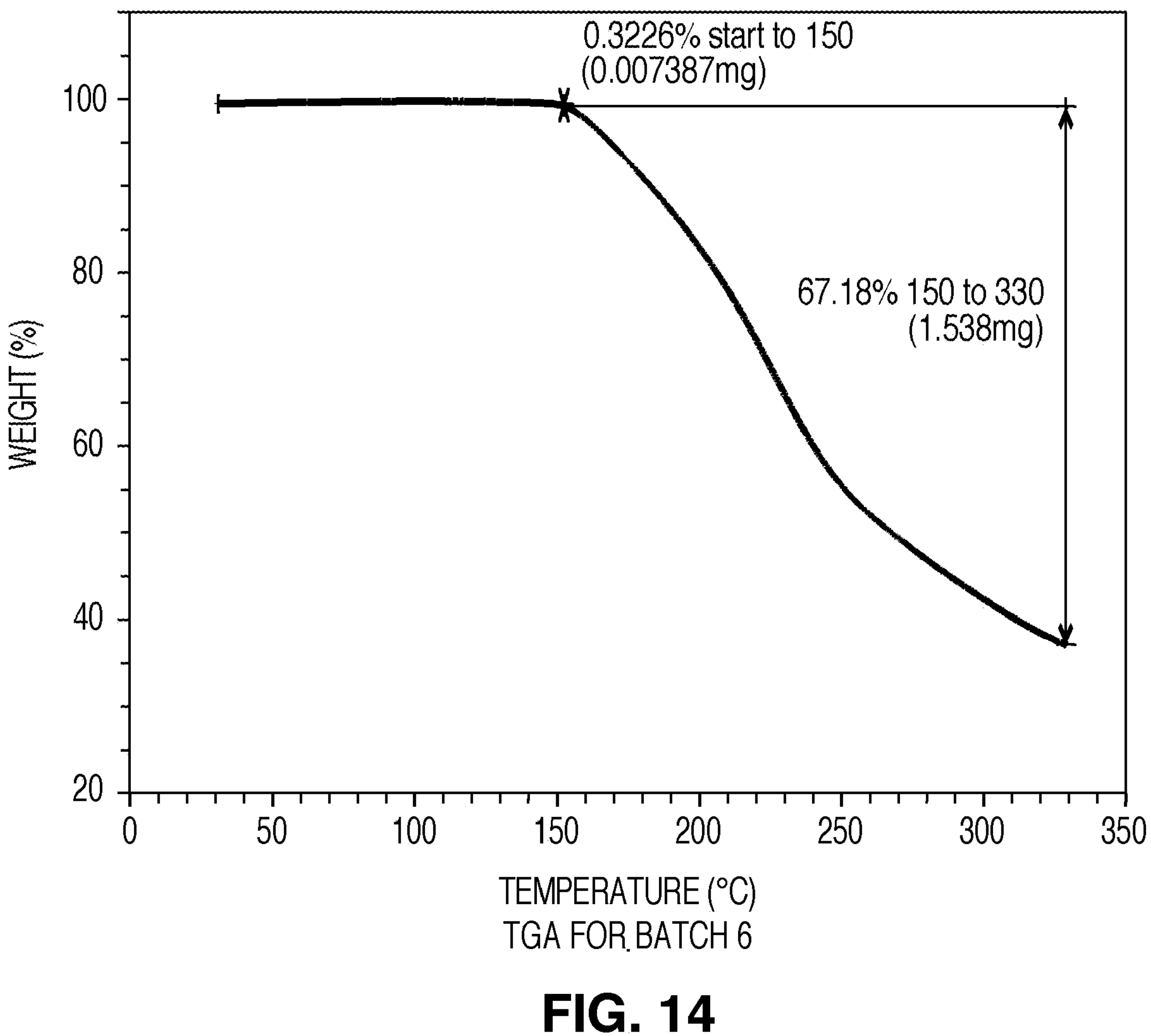
FIG. 14 provides Thermogravimetric Analysis (TGA) of a spray dried powder produced from 2380 mg of mannitol dissolved in 70 ml of water and 1400 mg of bendamustine in 70 ml of n-propanol.
Figure 15:
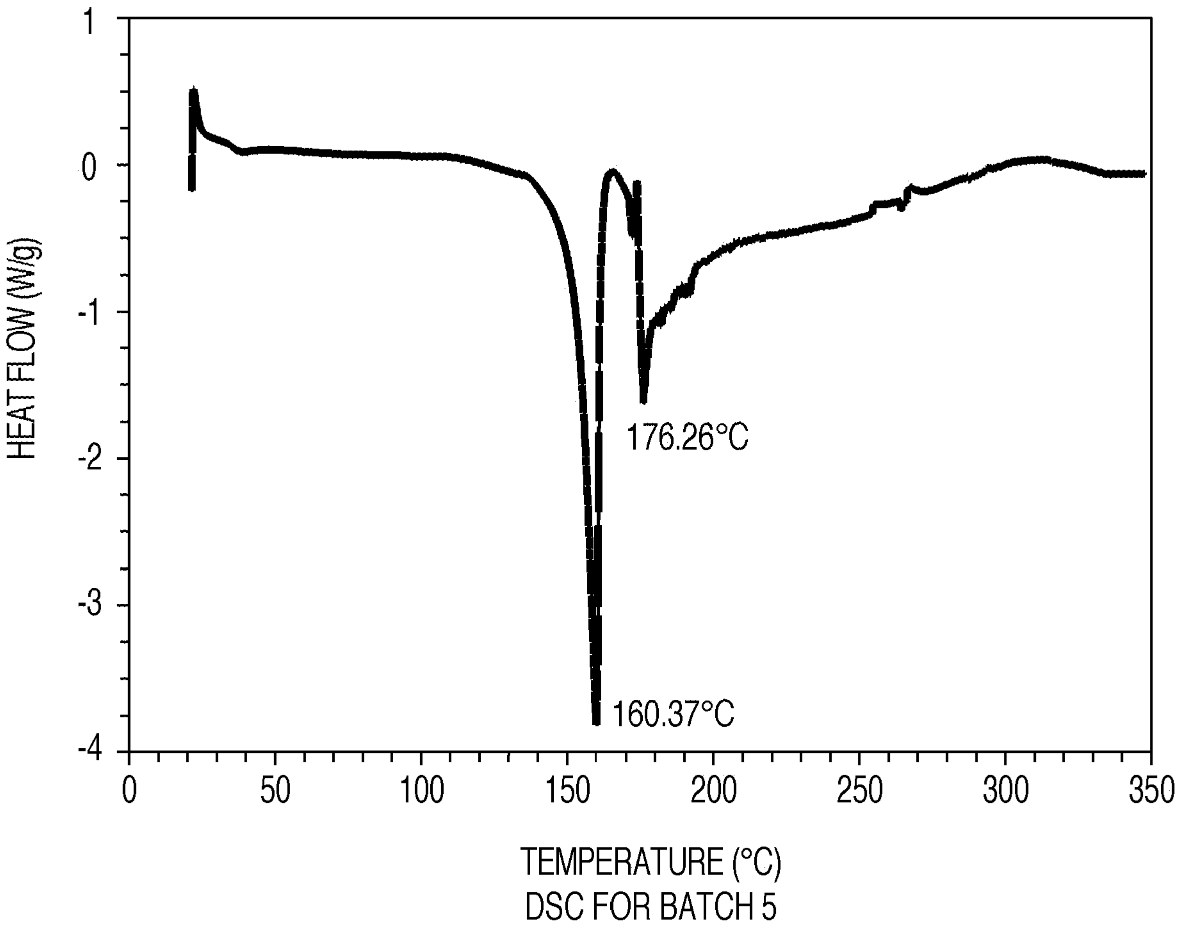
FIG. 15 provides Differential Scanning calorimetry (DSC) of a spray dried powder produced from 1190 mg of mannitol dissolved in 70 ml of water and 700 mg of bendamustine hydrochloride in 70 ml.

FIGS. 13 and 14 show the Thermogravimetric Analysis (TGA) for Batch 5 and 6 respectively. FIG. 15 shows Differential Scanning Calorimetry (DSC) results for Batch 5.

TABLE 10

| Prominent peaks for Batch 6. | | |
|---|---|---|
| 2θ | d space (Å) | Intensity (%) |
| 9.76 ± 0.2 | 9.058 ± 0.185 | 35 |
| 13.74 ± 0.2 | 6.439 ± 0.093 | 33 |
| 17.35 ± 0.2 | 5.107 ± 0.058 | 65 |
| 18.80 ± 0.2 | 4.715 ± 0.050 | 45 |
| 19.91 ± 0.2 | 4.456 ± 0.044 | 66 |
| 20.48 ± 0.2 | 4.334 ± 0.042 | 100 |
| 21.34 ± 0.2 | 4.161 ± 0.039 | 68 |
| 22.16 ± 0.2 | 4.008 ± 0.036 | 30 |
| 24.73 ± 0.2 | 3.597 ± 0.029 | 29 |
| 25.29 ± 0.2 | 3.519 ± 0.027 | 40 |
| 27.07 ± 0.2 | 3.291 ± 0.024 | 26 |
| 27.57 ± 0.2 | 3.233 ± 0.023 | 24 |
| 28.21 ± 0.2 | 3.161 ± 0.022 | 31 |
| 33.22 ± 0.2 | 2.695 ± 0.016 | 22 |
| 34.04 ± 0.2 | 2.631 ± 0.015 | 19 |
| 35.62 ± 0.2 | 2.518 ± 0.014 | 18 |
| 36.23 ± 0.2 | 2.478 ± 0.013 | 29 |
| 39.63 ± 0.2 | 2.272 ± 0.011 | 16 |

TABLE 10-continued

Example 6: Reconstitution Experiments

Dry powder containing 25 mg of Bendamustine Hydrochloride API, obtained from each one of Batches 1 to 6 was added to an appropriately sized transparent container. 5 ml of water was, subsequently, added into the container and the container was sealed and shaken for approximately 20 seconds. The solutions were then allowed to settle. The transparency of the solutions was assessed by visual observation 2 and 3 minutes after the addition of water. In all cases the solutions were transparent and no particulates were observed indicating complete dissolution of the dry powder in water.

All of the compositions and methods disclosed and claimed herein can be made and executed without undue experimentation in light of the present disclosure. While the compositions and methods have been described in terms of preferred embodiments, it will be apparent to those of skill in the art that variations can be applied to the compositions and methods and in the steps or in the sequence of steps of the method described herein without departing from the spirit and scope. More specifically, it will be apparent that certain solvents which are both chemically and physiologically related to the solvents disclosed herein can be substituted for the solvents described herein while the same or similar results would be achieved. All such similar substitutes and modifications apparent to those skilled in the art are deemed to be within the spirit and scope as defined by the appended claims.

All patents, patent applications, and publications mentioned in the specification are indicative of the levels of those of ordinary skill in the art to which the specification pertains. All publications and patent, applications cited in this specification are herein incorporated by reference as if each individual publication or patent application were specifically and individually indicated to be incorporated by reference.

The embodiments illustratively described herein suitably can be practiced in the absence of any element(s) not specifically disclosed herein. Thus, for example, in each instance herein any of the terms "comprising", "consisting essentially of", and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope claimed. Thus, it should be understood that although the present embodiments have been specifically disclosed by preferred embodiments and optional features, modification and variation of the concepts herein disclosed can be resorted to by those skilled in the art, and that such modifications and variations are considered to be within the scope as defined by the appended claims. Accordingly, it is intended that the scope of the subject matter limited solely by the scope of the following claims, including equivalents thereof.

What is claimed is:

1. A spray-dried solid dispersion comprising a nitrogen mustard compound, or a pharmaceutically acceptable salt thereof, and one or more pharmaceutically acceptable excipients, diluents, or carriers, wherein the nitrogen mustard compound is selected from the group consisting of bendamustine, bestrabucil, chlorambucil, cyclophosphamide, diphenylspiromustine, spiromustine, melphalan, estramustine phosphate sodium, ifosfamide, mafosfamide, and prednimustine, wherein the spray-dried solid dispersion is substantially free of hydrolysis degradants of the nitrogen mustard compound, or a pharmaceutically acceptable salt thereof, wherein the spray-dried solid dispersion comprises less than 8% by weight water, and wherein the spray-dried solid dispersion is used in a method of treating a medical condition selected from a group including chronic lymphocytic leukemia (CLL), Hodgkin's disease, non-Hodgkin's lymphoma (NHL), multiple myeloma (MM), breast cancer, small cell lung cancer, hyperproliferative disorders, and autoimmune diseases.

* * * * *